US009518264B2

(12) United States Patent
Monteleone

(10) Patent No.: US 9,518,264 B2
(45) Date of Patent: Dec. 13, 2016

(54) ANTISENSE OLIGONUCLEOTIDES (ODN) AGAINST SMAD7 AND USES THEREOF IN MEDICAL FIELD

(71) Applicant: Nogra Pharma Limited, Dublin (IE)

(72) Inventor: Giovanni Monteleone, Grottaferrata (IT)

(73) Assignee: Nogra Pharma Limited, Dublin (IE)

( * ) Notice: Subject to any disclaimer, the term of this patent is extended or adjusted under 35 U.S.C. 154(b) by 0 days.

(21) Appl. No.: 15/201,061

(22) Filed: Jul. 1, 2016

(65) Prior Publication Data

US 2016/0304876 A1    Oct. 20, 2016

Related U.S. Application Data

(60) Continuation of application No. 14/815,339, filed on Jul. 31, 2015, now Pat. No. 9,382,541, which is a continuation of application No. 14/613,181, filed on Feb. 3, 2015, now Pat. No. 9,096,854, which is a continuation of application No. 14/144,029, filed on Dec. 30, 2013, now Pat. No. 9,006,418, which is a continuation of application No. 13/836,634, filed on Mar. 15, 2013, now Pat. No. 8,648,186, which is a continuation of application No. 13/332,134, filed on Dec. 20, 2011, now abandoned, which is a continuation of application No. 12/854,558, filed on Aug. 11, 2010, now Pat. No. 8,106,182, which is a continuation of application No. 12/264,058, filed on Nov. 3, 2008, now Pat. No. 7,807,818, which is a division of application No. 11/501,756, filed on Aug. 10, 2006, now abandoned, which is a continuation-in-part of application No. 10/551,643, filed as application No. PCT/IT2004/000117 on Mar. 8, 2004, now Pat. No. 7,700,757.

(30) Foreign Application Priority Data

Apr. 2, 2003    (IT) .............................. RM2003A0149

(51) Int. Cl.
*C07H 21/04*    (2006.01)
*C12N 15/113*    (2010.01)

(52) U.S. Cl.
CPC ....... *C12N 15/1136* (2013.01); *C12N 2310/11* (2013.01); *C12N 2310/315* (2013.01); *C12N 2310/3341* (2013.01); *C12N 2310/344* (2013.01); *C12N 2310/3521* (2013.01)

(58) Field of Classification Search
None
See application file for complete search history.

(56) References Cited

U.S. PATENT DOCUMENTS

| | | |
|---|---|---|
| 5,654,004 A | 8/1997 | Okayama et al. |
| 5,783,566 A | 7/1998 | Mislick |
| 5,856,462 A | 1/1999 | Agrawal |
| 5,874,416 A | 2/1999 | Sheikhnejad |
| 5,929,226 A | 7/1999 | Padmapriya et al. |
| 5,962,673 A | 10/1999 | Monia et al. |
| 6,020,464 A | 2/2000 | Okazaki et al. |
| 6,096,722 A | 8/2000 | Bennett et al. |
| 6,159,697 A | 12/2000 | Monia et al. |
| 6,200,602 B1 | 3/2001 | Watts et al. |
| 6,228,642 B1 | 5/2001 | Baker et al. |
| 6,251,628 B1 | 6/2001 | Nakao et al. |
| 6,455,689 B1 | 9/2002 | Schlingensiepen et al. |
| 6,479,465 B2 | 11/2002 | Strober et al. |
| 6,605,443 B1 | 8/2003 | Nakao et al. |
| 6,613,751 B2 | 9/2003 | Raz et al. |
| 6,747,014 B2 | 6/2004 | Teng et al. |
| 6,794,367 B1 | 9/2004 | Tanida et al. |
| 6,884,787 B2 | 4/2005 | Monia et al. |
| 6,943,241 B2 | 9/2005 | Isogai et al. |
| 7,485,627 B2 | 2/2009 | Raz et al. |
| 7,667,027 B2 | 2/2010 | Schlingensiepen et al. |
| 7,700,572 B2 | 4/2010 | Steinbrecher et al. |
| 7,700,757 B2 | 4/2010 | Monteleone |
| 7,807,818 B2 | 10/2010 | Monteleone |
| 8,106,182 B2 | 1/2012 | Monteleone |
| 8,110,355 B2 | 2/2012 | Atwood et al. |
| 8,648,186 B2 | 2/2014 | Monteleone |
| 8,907,078 B2 | 12/2014 | Monteleone |
| 8,912,154 B2 | 12/2014 | Baroni et al. |
| 9,006,418 B2 | 4/2015 | Monteleone |
| 9,096,854 B1 | 8/2015 | Monteleone |
| 9,279,126 B2 | 3/2016 | Monteleone |
| 9,314,434 B2 | 4/2016 | Baroni et al. |

(Continued)

FOREIGN PATENT DOCUMENTS

| | | |
|---|---|---|
| EP | 0874046 | 10/1998 |
| EP | 1308459 | 5/2003 |

(Continued)

OTHER PUBLICATIONS

Affidavit of Dr. Doug Kornbrust, Ph.D., dated Apr. 15, 2009; Re: Canadian Patent Application No. 20042520541 titled "Antisense Oligonucleotides (ODN) Against Smad7 and Uses in Medical Field Thereof."
Affidavit of Francesca Viti, Ph.D., dated 2009; Re: Canadian Patent Application No. 20042520541 titled "Antisense Oligonucleotides (ODN) Against Smad7 and Uses in Medical Field Thereof."
Agrawal et al. (2000) "Antisense Therapeutics: Is it as Simple as Complementary Base Recognition?," *Molecular Medicine Today* 6:72-81.
Anitescu et al., "Interleukin-10 Functions in Vitro and in Vivo to Inhibit Bacterial DNA-Induced Secretion of Interleukin-12," Journal of Interferon and Cytokine Research, vol. 17, pp. 781-788 (1997).

(Continued)

*Primary Examiner* — Kimberly Chong
(74) *Attorney, Agent, or Firm* — Goodwin Procter LLP

(57) ABSTRACT

The invention relates to antisense oligonucleotidic sequences (ODN) against Smad7 suitably modified, and their uses in medical field as therapeutic biological agents, in particular in the treatment of chronic inflammatory bowel disease, such as Crohn's disease and ulcerative colitis.

3 Claims, 10 Drawing Sheets

(56) References Cited

U.S. PATENT DOCUMENTS

| | | |
|---|---|---|
| 9,382,541 B2 | 7/2016 | Monteleone |
| 2002/0034736 A1 | 3/2002 | Falb et al. |
| 2002/0061569 A1 | 5/2002 | Haselbeck et al. |
| 2002/0147140 A1 | 10/2002 | Rosen et al. |
| 2002/0177568 A1 | 11/2002 | Stinchcomb et al. |
| 2003/0049662 A1 | 3/2003 | Monia et al. |
| 2004/0209805 A1 | 10/2004 | Phillips et al. |
| 2004/0265833 A1 | 12/2004 | Lofton-Day et al. |
| 2005/0119203 A1 | 6/2005 | Steinbrecher et al. |
| 2006/0034800 A1 | 2/2006 | Sanna et al. |
| 2007/0042985 A1 | 2/2007 | Monteleone |
| 2007/0155685 A1 | 7/2007 | Schlingensiepen et al. |
| 2007/0167385 A1 | 7/2007 | Monteleone |
| 2008/0015160 A1 | 1/2008 | Inazawa et al. |
| 2008/0214483 A1 | 9/2008 | Schlingensiepen et al. |
| 2008/0312093 A1 | 12/2008 | Inazawa et al. |
| 2009/0156539 A1 | 6/2009 | Monteleone |
| 2010/0317719 A1 | 12/2010 | Monteleone |
| 2011/0152352 A1 | 6/2011 | Hata et al. |
| 2011/0207795 A1 | 8/2011 | Steinbrecher et al. |
| 2012/0015033 A1 | 1/2012 | Baroni et al. |
| 2012/0136043 A1 | 5/2012 | Monteleone |
| 2013/0203839 A1 | 8/2013 | Monteleone |
| 2014/0142163 A1 | 5/2014 | Monteleone |
| 2014/0256788 A1 | 9/2014 | Monteleone |
| 2014/0271860 A1 | 9/2014 | Monteleone et al. |
| 2015/0125523 A1 | 5/2015 | Baroni et al. |
| 2015/0148245 A1 | 5/2015 | Monteleone et al. |
| 2015/0211011 A1 | 7/2015 | Monteleone |
| 2015/0232854 A1 | 8/2015 | Baroni et al. |
| 2015/0315573 A1 | 11/2015 | Monteleone et al. |
| 2015/0337312 A1 | 11/2015 | Monteleone |

FOREIGN PATENT DOCUMENTS

| | | |
|---|---|---|
| EP | 1608753 B1 | 12/2008 |
| EP | 1456380 B1 | 4/2012 |
| WO | WO-97/30065 | 8/1997 |
| WO | WO-98/53068 | 11/1998 |
| WO | WO-99/50296 | 10/1999 |
| WO | WO-99/60012 | 11/1999 |
| WO | WO-00/06206 | 2/2000 |
| WO | WO-01/53313 A1 | 7/2001 |
| WO | WO-01/55367 | 8/2001 |
| WO | WO-01/57182 | 8/2001 |
| WO | WO-01/94629 | 12/2001 |
| WO | WO-02/00927 | 1/2002 |
| WO | WO-02/12440 | 2/2002 |
| WO | WO-02/068579 | 9/2002 |
| WO | WO-02/077183 | 10/2002 |
| WO | WO-02/085285 | 10/2002 |
| WO | WO-03/037368 | 5/2003 |
| WO | WO-2004/041170 | 5/2004 |
| WO | WO-2004/053099 | 6/2004 |
| WO | WO-2004/083389 | 9/2004 |
| WO | WO-2004/087920 | 10/2004 |
| WO | WO-2005/012875 | 2/2005 |
| WO | WO-2005/014011 | 2/2005 |
| WO | WO-2005/049642 | 6/2005 |
| WO | WO-2005/077403 | 8/2005 |
| WO | WO-2005/098041 | 10/2005 |
| WO | WO-2007/022642 | 3/2007 |
| WO | WO-2007/099345 A1 | 9/2007 |
| WO | WO-2007/120847 | 10/2007 |
| WO | WO-2008/014400 A2 | 1/2008 |
| WO | WO-2008/046964 A2 | 4/2008 |

OTHER PUBLICATIONS

Arsura et al. (1996) "TGFβ1 Inhibits N-κB/Rel Activity Inducing Apoptosis of B Cells: Transcriptional Activation of IκBα," *Immunity* 5:31-40.

Boirivant et al. (1998) "Oxazolone Colitis: A Murine Model of T Helper Cell Type 2 Colitis Treatable with Antibodies to Interleukin 4," *The Journal of Experimental Medicine* 188(10):1929-1939.

Boirivant et al. (1999) "Lamina Propria T Cells in Crohn's Disease and other Gastrointestinal Inflammation Show Defective CD2 Pathway-Induced Apoptosis," *Gastroenterology*, 116:557-565.

Boirivant et al. (2001) "Oral Administration of Recombinant Cholera Toxin Subunit B Inhibits IL-12-Mediated Murine Experimental (Trinitrobenzene Sulfonic Acid) Colitis," *The Journal of Immunology* 166(5):3522-3532.

Boirivant et al.(2006) "Inhibition of Smad7 With a Specific Antisense Oligonucleotide Facilitates TGF-β1-Mediated Supression of Colitis," *Gastroenterology* 131:1786-1798.

Calabresi et al. (1998) "Phase 1 Trial of Transforming Growth Factor Beta 2 in Chronic Progressive MS," *Neurology* 51(1):289-292.

Calastretti A. and Nicolin A. (1998) *Biotechnologie Farmacolpgiche* Cap. 8, pp. 125-131.

Canadian Intellectual Property Office Action dated Mar. 7, 2008; Canadian Application No. 2,520,541; Owner: Giuliani International Limited; Title: "Antisense Oligonucleotides (ODN) Against SMAD7 and Uses in Medical Field Thereof"; (Jan. 2006).

Canadian Intellectual Property Office Action dated Oct. 3, 2008, Canadian Application No. 2,520,541; Owner: Giuliani International Limited; Title: "Antisense Oligonucleotides (ODN) Against SMAD7 and Uses in Medical Field Thereof"; (Jan. 2006).

Canadian Intellectual Property Office Action dated Sep. 13, 2010, Canadian Application No. 2,520,541; Owner: Giuliani International Limited; Title: "Antisense Oligonucleotides (ODN) Against SMAD7 and Uses in Medical Field Thereof"; (Jan. 2006).

Celgene Corporation (2015) "Phase II Data for Celgene's Investigational Oral GED-0301 for Patients with Active Crohn's Disease Published in New England Journal of Medicine" (3 pages).

Christ et al. (1994) "Immune Dysregularation in TGF-β1-Deficient Mice," *The Journal of Immunology* 153(5):1936-1946.

Database EMBL Online, "Homo sapiens MAD-related Gene SMAD7 (SMAD7) mRNA, Complete CDS," Database Accession No. AF010193, Jul. 13, 1997 (3 pages).

EP Examination Report for Application No. 04 718 384.3 Aug. 2, 2007 (4 pages).

Fina et al., "Interleukin-25 Production is Differently Regulated by TNF-alpha and TGF-beta1 in the Human Gut," Mucosal Immunology, vol. 4, pp. 239-244 (2011).

Fiocchi, C. (2001) "TGF-β/Smad Signaling Defects in Inflammatory Bowel Disease: Mechanisms and Possible Novel Therapies for Chronic Inflammation," *The Journal of Clinical Investigation* 108(4):523-526.

Gilboa-Geffen et al., "Activation of the Alternative NFkB Pathway Improves Disease Symptoms in a Model of Sjogren's Syndrome," PLoS One, vol. 6, pp. 1-9 (2011).

Gorelik et al. (2000) "Abrogation of TGFβ Signaling in T Cells Leads to Spontaneous T Cell Differentiation and Autoimmune Disease," *Immunity* 12:171-181.

Gorelik et al. (2002) "Transforming Growth Factor-β in T-Cell Biology," *Nature Reviews/Immunology* 2(1):46-53.

Guerlavais et al. (2002) "Use of Maldi-TOF Mass Spectrometry to Monitor Solid-Phase Synthesis of Oligonucleotides," *Anal Bioanal Chem* 374:57-63.

Hahm et al. (2001) "Loss of Transforming Growth Factor β Signalling in the Intestine Contributes to Tissue Injury in Inflammatory Bowel Disease," *Gut* 49(2):190-198.

Han et al. (1998) "Transforming Growth Factor-Beta 1 (TGF-β1) Promotes IL-2 mRNA Expression Through the Up-regulation of NF-κB, AP-1 and NF-AT in EL4 Cells," *The Journal of Pharmacology and Experimental Therapeutics* 287(3):1105-1112.

Hayashi et al. (1997) "The MAD-related Protein Smad7 Associates with the TGFβ Receptor and Functions as an Antagonist of TGFβ Signaling," *Cell* 89(7):1165-1173.

Heldin et al. (1997) "TGF-β Signalling from Cell Membrane to Nucleus Through SMAD Proteins," *Nature* 390(6659):465-471.

Hohlfield et al. (2001) "The Ups and Downs of Multiple Schlerosis Therapeutics," *Annals of Neurology* 49(3):281-284.

(56) References Cited

OTHER PUBLICATIONS

International Search Report for International Application No. PCT/EP02/12221 completed on Sep. 2, 2003 (9 pages).

International Search Report for PCT/IT2004/000117, completed on Aug. 5, 2004 (3 pages).

Kiefer et al. (1998) "Sequential Expression of Transforming Growth Factor-β1 by T-cells, Macrophages, and Microglia in Rat Spinal Cord During Autoimmune Inflammation," *Journal of Neuropathology and Experimental Neurology* 57(5):385-395.

Kitani, et al. (2000) "Treatment of Experimental (Trinitrobenzene Sulfonic Acid) Colitis by Intranasal Administration of Transforming Growth Factor (TGF)-β1 Plasmid: TGF-β1-Mediated Supression of T Helper Cell Type 1 Response Occurs by Interleukin (IL)-10 Induction and IL-12 Receptor β2 Chain Downregulation," *The Journal of Experimental Medicine* 192(1): 41-52.

Krieg et al. (1995) "CpG motifs in bacterial DNA trigger direct B-cell activation," Nature 374(6522):546-549.

Krieg et al. (1999) "Mechanisms and applicaitons of immune stimulatory CpG oligodeoxynucleotides," *Biochimica et Biophysica Acta* 1489(1):107-116.

Kulkarni, et al. (1993) "Transforming Growth Factor-$\beta_1$ Knockout Mice, A Mutation in One Cytokine Gene Causes a Dramatic Inflammatory Disease," *American Journal of Pathology* 143(1): 3-9.

Landstrom et al. (2000) "Smad7 Mediates Apoptosis Induced by Transforming Growth Factor β in Prostatic Carcinoma Cells," *Current Biology* 10(9):535-538.

Lawrance et al. (2001) "Inflammation Location, But Not Type, Determines the Increase in TGF-β1 and IGF-1 Expression and Collagen Deposition in IBD Intestine," *Inflammatory Bowel Diseases* 7(1):16-26.

Lawrance et al. (2003) "A Murine Model of Chronic Inflammation-Induced Intestinal Fibrosis Down-Regulated by Antisense NF-κB," *Gastroenterology* 125(6):1750-1761.

Lesiak et al. (1993) "2',5'-Oligoadenylate: Antisense Chimeras—Synthesis and Properties," *Bioconjugate Chem.* 4(6):467-472.

Ludviksson et al. (1997) "TGF-β Production Regulates the Development of the 2,4,6-Trinitrophenol-Conjugated Keyhold Limpet Hemocyanin-Induced Colonic Inflammation in IL-2-Deficient Mice," *The Journal of Immunology* 159(1):3622-3628.

Mahato et al. (2005) "Modulation of Gene Expression by Antisense and Antigene Oligodeoxynucleotides and Small Interfering RNA," *Expert Opinion on Drug Delivery* 2(1)3-28.

Maier et al. (2000) "Synthesis of Chimeric Oligonucleotides Containing Phosphodiester, Phosphorothioate, and Phosphoramidate Linkages," *Organic Letters* 2(13)1819-1822.

Marafini et al., "TGF-Beta Signaling Manipulation as Potential Therapy for IBD," Current Drug Targets, vol. 14, pp. 1400-1404 (2013).

Massagué, J. (2000) "How Cells Read TGF-β Signals," *Nature Reviews Molecular Cell Biology* 1(3):169-178.

Miyazono et al. (2001) "Divergence and Convergence of TGF-β/BMP Signaling," *Journal of Cellular Physiology* 187(3):265-276.

Mokhtarian et al. (1994) "Defective Production of Anti-Inflammatory Cytokine, TFG-β by T Cell Lines of Patients with Active Multiple Sclerosis," *Journal of Immunology* 152(12):6003-6010.

Monteleone et al. (2001) "Blocking Smad7 Restores TGF-β1 Signaling in Chronic Inflammatory Bowel Disease," *The Journal of Clinical Investigation* 108(4):601-609.

Monteleone et al. (2004) "A Failure of Transforming Growth Factor-B1 Negative Regulation Maintains Sustained NF-κB Activation in Gut Inflammation," *The Journal of Biological Chemistry* 279(6):3925-3932.

Monteleone et al. (2004) "Induction and Regulation of Smad7 in the Gastric Mucosa of Patients with Helicobacter Pylori Infection," *Gastroenterology* 126(3)674-682.

Monteleone et al. (2004) "Smad7 in TGF-B-Mediated Negative Regulation of Gut Inflammation," *Trends in Immunology* 25(10):513-517.

Monteleone et al. (2005) "Post-Transcriptional Regulation of Smad7 in the Gut of Patients with Inflammatory Bowel Disease," *Gastroenterology* 129(5):1420-1429.

Monteleone et al., (2015) "Mongersen, an Oral SMAD7 Antisense Oligonucleotide, and Crohn's Disease" *N Engl J Med* 372 (12):1104-1113.

Monteleone, et al. (2008) "TGF-62 1 and SMAD7 in the Regulation of IBD," *Mucosal Immunol.* 1(1): S50-S53.

Monteleone, et al. (2012) "Phase I Clinical Trial of SMAD7 Knockdown Using Antisense Oligonucleotide in Patients with Active Crohn's Disease," *Molecular Therapy* 20: 870-876.

Moseman et al., "Human Plasmacytoid Dendritic Cells Activated by CpG Oligodeoxynucleotides Induce the Generation of CD4+CD25+Regulatory T Cells[1.]" The Journal of Immunology, pp. 4433-4442 (2004).

Nakao et al. (1997) "Identification of Smad7, a TGF-α inducible antagonist of TGF-α signalling" *Nature* 389(6651):631-635.

Nakao et al. (2002) "Expression of Smad7 in Bronchial Epithelial Cells is Inversely Correlated to Basement Membrane Thickness and Airway Hyperresponsiveness in Patients with Asthma," *J Allergy Clin. Immunol.* 110(6):873-878.

Nakao et al., "Smad7: A New Key Player in TGF-Beta-Associated Disease," Trends in Molecular Medicine, vol. 8, pp. 361-363 (2002).

Neurath et al. (1996) "Experimental Granulomatous Colitis in Mice is Abrogated by Induction of TGF-β-Medicated Oral Tolerance," *J. Exp. Med.* 183(6):2605-2616.

Neurath et al. (2000) "TNBS-Colitis," *Intern. Rev. Immunol.* 19(1):51-62.

Nguyen et al. (2008) "RNAi Therapeutics: An Update on Delivery," *Current Opinion in Molecular Therapeutics* 10(2):158-167.

Okado et al. (2002) "Smad7 Mediates Transforming Growth Factor-B-Induced Apoptosis in Mesangial Cells," *Kidney International* 62(4):1178-1186.

Podolsky, D.K. (2002) "Inflammatory Bowel Disease," *N. Engl. J. Med.* 347(6):417-429.

Powrie et al. (1996) "A Critical Role for Transforming Growth Factor-β but Not Interleukin 4 in the Suppression of T Helper Type 1-mediated Colitis by CD45RBlow CD4+ T Cells," *J. Exp. Med.* 183(6): 2669-2674.

Prud'Homme et al. (2000) "The Inhibitory Effects of Transforming Growth Factor-Beta-1 (TGF-β-1) in Autoimmune Diseases," *Journal of Autoimmunity* 14(1):23-42.

Ragas et al. (2000) "A Comparative Study on Methods of Optimal Sample Preparation for the Analysis of Oligonucleotides by Matrix-Assisted Laser Desorption/Ionization Mass Spectrometry," *Analyst* 125(4):575-581.

Rayburn et al. (2008) "Antisense RNAi, and Gene Silencing Strategies for Therapy: Mission Possible or Impossible?," *Drug Discovery Today* 13(11-12):513-521.

Read et al. (2001) "Induction of Inflammatory Bowel Disease in Immunodeficient Mice by Depletion of Regulatory T Cells," Current Protocols in Immunology 15.13.1-15.13.10.

Redford et al., "Cyclosporin A Enhances IL-12 Production by CpG Motifs in Bacterial DNA and Synthetic Oligodeoxynucleotides," The American Association of Immunologists, pp. 3930-3935 (1998).

Samarakoon, et al. (2013) "TGF-b Signaling in Tissue Fibrosis: Redox Controls, Target Genes and Therapeutic Opportunities," *Cellular Signalling* 25: 264-268.

Sanborn et al. (2002) "Biologic Therapy of Inflammatory Bowel Disease," Gastroenterology 122(6)1592-1608.

Sanghvi et al. (1993) "Antisense Oligodeoxynucleotides: Synthesis, Biophysical and Biological Evaluation of Oligodeoxynucleotides Containing Modified Pyrimidines," *Nucleic Acids Research* 21(14):3197-3203.

Scherer et al. (2003) "Approaches for the Sequence-Specific Knockdown of mRNA," *Nat. Biotechnol.* 21(12):1457-1465.

Seegers et al. (2002) "Review Article: A Critical Approach to New Forms of Treatment of Crohn's Disease and Ulcerative Colitis," Aliment Pharmacol Ther 16(4):53-58.

(56) References Cited

OTHER PUBLICATIONS

Shull et al. (1992) "Targeted Disruption of the Mouse Transforming Growth Factor-b1 Gene Results in Multifocal Inflammatory Disease," *Nature* 359(6397):693-699.

Soilu-Hanninen et al. (2000) "Treatment of Experimental Autoimmune Encephalomylitis with Antisense Oligonucleotides Against the Low Affinity Neurotrophin Receptor," *Journal of Neuroscience Research* 59(6):712-721.

Soto et al. (2003) "SMAD2 and SMAD7 Involvement in the Post-translational Regulation of Muc4 via the Transforming Growth Factor-B and Interferon-y Pathways in Rat Mammary Epithelial Cells," *The Journal of Biological Chemistry*, 278(22):20338-20344.

Souchelnytskyi et al. (1998) "Physical and Functional Interaction of Murine and Xenopus Smad7 with Bone Morphogenetic Protein Receptors and Transforming Growth Factor-β Receptors," *The Journal of Biological Chemistry* 273(39):25364-25370.

Steinbrecher et al. (2001) "Targeting Dipeptidyl Peptidase IV (CD26) Suppresses Autoimmune Encephalomyelitis and Up-Regulates TGF-β1 Secretion in Vivo," *Journal of Immunology* 166(3)2041-2048.

Stopa et al. (2000) "Genomic Locus and Promoter Region of Rat Smad7, an important antagonlis of TGF-β signaling," *Mammalian Genome* 11(2):169-176.

Stopa et al. (2000) "Participation of Smad2, Smad3, and Smad4 in transforming growth factor β (TGF-β)—induced activation of Smad7: the TGF-β response element of the promoter requires functional Smad binding element and E-box sequences for transcriptional regulation," *J. of Biological Chemistry* 275(38):29308-29317.

Vermeire, S. (2015) "Oral SMAD7 Antisense Drug for Crohn's Disease" *N Engl J Med* 372(12):1166-1167.

Vollmer et al., "Highly Immunostimulatory CpG-Free Oligodeoxynucleotides for Activation of Human Leukocytes," *Antisense & Nucleic Acid Drug Development*, vol. 12, pp. 165-175 (2002).

Volpi et al., "A GpC-Rich Oligonucleotide Acts on Plasmacytoid Dendritic Cells to Promote Immune Suppression," *The Journal of Immunology*, pp. 2283-2289 (2012).

Volpi et al., "High Doses of CpG Oligodeoxynucleotides Stimulate a Tolerogenic TLR9-TRIF Pathway," Nature Communications, pp. 1-11 (2013).

Wiendl et al. (2000) "Multiple Sklerose, Aktuelle Obersicht zu Fehlgeschlagenen and Abgebrochenen Therapiestudien," *Nervenarzt* 71(8):597-610.

Xiao et al. (1996) "Synthesis and Characterization of Composite Nucleic Acids Containing 2',5'-Oligoriboadenylate Linked to Antisense DNA," *Antisense & Nucleic Acid Drug Development* 6(4):247-258.

Yang et al. (1999) "Targeted Disruption of SMAD3 Results in Impaired Mucosal Immunity and Diminished T Cell Responsiveness to TGF-β," *The EMBO Journal* 18(5):1280-1291.

Zhang et al. (2004) "Targeted Gene Silencing by Small Interfering RNA-Based Knock-Down Technology," *Current Pharmaceutical Biotechnology* 5(1):1-7.

Zhang et al. (2008) "microRNAs: A New Emerging Class of Players for Disease Diagnostics and Gene Therapy," *J. Cell. Mol. Med.* 12(1):3-21.

Zorzi et al. (2012) "A Phase 1 Open-Label Trial Shows that SMAD7 Antisense Oligonucleotide (GED0301) Does Not Increase the Risk of Small Bowel Strictures in Crohn's Disease," *Alimentary Pharmacology and Therapeutics* 36: 850-857.

N.S.

ODN Sense

ODN Antisense

SEQUENCE LISTING

<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtcgcccctt ctccccgcag c                                                 21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: cytosine, 5-methylcytosine, or
      2'-O-methylcytosine
<220> FEATURE:
<221> NAME/KEY: modified_base
<222> LOCATION: (4)
<223> OTHER INFORMATION: guanine, 5-methylguanine, or 2'-O-methylguanine
<220> FEATURE:
<221> NAME/KEY: modified_base
<222> LOCATION: (16)
<223> OTHER INFORMATION: cytosine, 5-methylcytosine, or
      2'-O-methylcytosine
<220> FEATURE:
<221> NAME/KEY: modified_base
<222> LOCATION: (17)
<223> OTHER INFORMATION: guanine, 5-methylguanine, or 2'-O-methylguanine

<400> SEQUENCE: 2 gtnnccccctt ctcccnncag                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 5-methyl 2'-deoxycytidine 5'-monophosphate
<220> FEATURE:
<221> NAME/KEY: modified_base
<222> LOCATION: (16)
<223> OTHER INFORMATION: 5-methyl 2'-deoxycytidine 5'-monophosphate

<400> SEQUENCE: 3
gtngcccctt ctcccngcag                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: 2'-deoxyguanosine methylphosphonate

```
<220> FEATURE:
<221> NAME/KEY: modified_base
<222> LOCATION: (3)
<223> OTHER INFORMATION: 5-methyl 2'-deoxycitidine 5'-monophosphate
<220> FEATURE:
<221> NAME/KEY: modified_base
<222> LOCATION: (16)
<223> OTHER INFORMATION: 5-methyl 2'-deoxycitidine 5'-monophosphate
<220> FEATURE:
<221> NAME/KEY: modified_base
<222> LOCATION: (20)
<223> OTHER INFORMATION: 2'-deoxyguanosine methylphosphonate

<400> SEQUENCE: 4
ntngcccctt ctcccngcan                                         20

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtttggtcct gaacatgc                                           18

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtttggtcct gaacat                                             16

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gtttggtcct gaacatg                                            17

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agcaccgagt gcgtgagc                                           18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (1)
<223> OTHER INFORMATION: 2'-deoxyadenosine methylphosphonate
<220> FEATURE:
<221> NAME/KEY: modified_base
<222> LOCATION: (6)
<223> OTHER INFORMATION: 5-methyl 2' deoxycitidine 5' monophosphate
<220> FEATURE:
<221> NAME/KEY: modified_base
<222> LOCATION: (12)
<223> OTHER INFORMATION: 5-methyl 2' deoxycitidine 5' monophosphate
<220> FEATURE:
<221> NAME/KEY: modified_base
<222> LOCATION: (18)
<223> OTHER INFORMATION: 2'-deoxycytosine methylphosphonate

<400> SEQUENCE: 9
ngcacngagt gngtgagn                                                18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cgaacatgac ctccgcac                                                18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: 5-methyl 2' deoxycitidine 5' monophosphate
<220> FEATURE:
<221> NAME/KEY: modified_base
<222> LOCATION: (14)
<223> OTHER INFORMATION: 5-methyl 2' deoxycitidine 5' monophosphate

<400> SEQUENCE: 11
ngaacatgac ctcngcac                                                18

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 5-methyl 2' deoxycitidine 5' monophosphate
<220> FEATURE:
<221> NAME/KEY: modified_base
<222> LOCATION: (16)
<223> OTHER INFORMATION: 5-methyl 2' deoxycitidine 5' monophosphate

<400> SEQUENCE: 12
gtngcccctt ctcccngcag                                              20

<210> SEQ ID NO 13
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 13
gatcgtttgg tcctgaa                                                      17

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atcgtttggt cctgaac                                                      17

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: 2'-deoxyguanosine methylphosphonate
<220> FEATURE:
<221> NAME/KEY: modified_base
<222> LOCATION: (3)
<223> OTHER INFORMATION: 5-methyl 2'-deoxycytidine 5'-monophosphate
<220> FEATURE:
<221> NAME/KEY: modified_base
<222> LOCATION: (16)
<223> OTHER INFORMATION: 5-methyl 2'-deoxycytidine 5'-monophosphate
<220> FEATURE:
<221> NAME/KEY: modified_base
<222> LOCATION: (20)
<223> OTHER INFORMATION: 2'-deoxyguanosine methylphosphonate

<400> SEQUENCE: 15 ntngccoctt ctcccngcan c                                                 21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 5-methyl 2'-deoxycitidine 5' monophosphate
<220> FEATURE:
<221> NAME/KEY: modified_base
<222> LOCATION: (17)
<223> OTHER INFORMATION: 5-methyl 2'-deoxycytidine 5'-monophosphate

<400> SEQUENCE: 16
gtngcccctt ctcccngcag c                                                 21
```

ANTISENSE OLIGONUCLEOTIDES (ODN) AGAINST SMAD7 AND USES THEREOF IN MEDICAL FIELD

CROSS-REFERENCE TO RELATED APPLICATIONS

This application is a continuation of U.S. application Ser. No. 14/815,339, filed Jul. 31, 2015, which is a continuation of U.S. application Ser. No. 14/613,181, filed Feb. 3, 2015 (issued as U.S. Pat. No. 9,096,854), which is a continuation of U.S. application Ser. No. 14/144,029, filed Dec. 30, 2013 (issued as U.S. Pat. No. 9,006,418), which is a continuation of U.S. application Ser. No. 13/836,634, filed Mar. 15, 2013 (issued as U.S. Pat. No. 8,648,186), which is a continuation of U.S. application Ser. No. 13/332,134, filed Dec. 20, 2011 (now abandoned), which is a continuation of U.S. application Ser. No. 12/854,558, filed Aug. 11, 2010 (issued as U.S. Pat. No. 8,106,182), which is a continuation of U.S. application Ser. No. 12/264,058, filed Nov. 3, 2008 (issued as U.S. Pat. No. 7,807,818), which is a divisional of U.S. application Ser. No. 11/501,756, filed Aug. 10, 2006 (now abandoned), which is a continuation-in-part of U.S. application Ser. No. 10/551,643, filed Jul. 24, 2006 (issued as U.S. Pat. No. 7,700,757), which is the national phase of International Patent Application No. PCT/IT2004/000117, filed Mar. 8, 2004, which claims priority to Italian Patent Application No. RM2003 A 000149, filed Apr. 2, 2003, the entire disclosure of each of which is incorporated by reference herein.

The present invention relates to antisense oligonucleotides (ODN) against Smad7 and uses thereof in medical field.

Particularly the invention refers to Smad7 antisense ODN sequences suitably modified, which show a surprising biological activity of specific inhibition of Smad7 expression and are therefore usable in medical field as therapeutic biological agents, in particular in the treatment of chronic inflammatory bowel disease (IBD).

Crohn's disease (CD) and ulcerative colitis (UC) are the major forms of chronic inflammatory bowel disease in human. Both diseases are complex clinical entities, whose pathogenesis is strictly dependent on the interaction between different genetic, environmental and immune factors.

Despite CD and UC show marked differences both on the pathophysiological and clinical level, the therapeutic approach to suffering patients shares many common elements. Variability of the clinical presentation, of the type and the extension of the lesions, and of the kind of complications influences the therapeutic choice, even though the pharmacological treatment would represent the first predominant approach.

Salicylazosulfapyridine and 5-aminosalicylic acid are drugs of proven efficacy in the management of the mild form of IBD and in the remission maintenance therapy.

In the phases with moderate to severe activity and in the cases in which the general state is involved, it is necessary to turn to the use of corticosteroids. From the medium and long-term analysis of the main worldwide case histories, it appears that clinical remission is obtainable only in two thirds of patients receiving corticosteroids, and only in 50% of these patients it does not occur any relapse after drugs suspension.

The continuous administering of corticosteroids, beside inducing drugs dependence phenomenon, is worsened due to a very high risk of side effects.

Also immunosuppressive treatment, which often accompanies or replaces corticosteroidal therapy, does not always ensure phlogosis containment and control of symptoms, and further has the disadvantages of numerous contraindications and severe side effects (Podolsky, 2002).

The new drug generation that became available in the 1990's, are biological agents. The more in-depth knowledge of IBD natural history and of the main pathophysiological mechanisms has contributed to steer medical intervention in a concrete way. Thus, a development of biotherapies aimed at controlling specific inflammatory "pathways" occurred through the use of recombinant human proteins, monoclonal chimeric humanized antibodies and fusion proteins. Contextually, agents which have showed a better efficacy in CD treatment are monoclonal chimeric antibodies directed to block TNF-α, a pro-inflammatory cytokine overproduced during IBD (Seegers et al., 2002). This compound, which is at present in phase IV of clinical trial, is effective in the inflammation containment in about 60-70% of the treated patients. Nevertheless, some side effects have been pointed out with a considerable frequency of incidence and recognizable in reactivation of latent microbial infections, hypersensitivity phenomena and formation of autoantibodies. The latter phenomenon could be based on the fact that anti-TNF-α neutralizes the cytokine TNF-α which has numerous biological functions.

In addition to its inflammatory effect, TNF-α takes part also to those mechanisms involved in the induction and maintaining of immunological tolerance. Therefore a block of TNF-α activity could paradoxically encourage excessive immunological reactions (Sandborn et al., 2002).

All these remarks suggest the need of new studies on animal models of IBD through which it is possible to identify new active principles to be used in a better and durable treatment of such pathologies (Fiocchi, 2001).

Anti-TNF-α treatment, as far as the other biotherapies, such as the administration of anti-inflammatory cytokines, for example IL-10, represents a therapeutic extracellular approach aimed at controlling biological effects of molecules secreted by inflammatory cells.

The study of the signal-transduction pathways activated by cytokine interaction with their receptors has outlined the chance to use new therapeutic strategies capable to modulate specifically and selectively the intracellular expression of important inflammatory and non inflammatory molecules.

Under normal conditions, the intestinal mucosa is the seat of a "physiological" inflammatory infiltrate, which is tightly controlled by various counter-regulatory mechanisms.

In relation to the above, an important role is played by TGF-β1, a multifunctional cytokine capable of regulating the growth, differentiation and activity of many immune and non immune cells.

Both in vitro and in vivo studies have demonstrated that TGF-β1 acts as a potent immunoregulator able to control mucosal intestinal inflammation, and that the inhibition of its activity results in the development of colitis which shows immunomorphological similarity with CD or UC (Powrie F. et al., 1996; Neurath M. F et al., 1996; Ludviksson B. R. et al., 1997).

In fact, TGF-β1 genes deficient mice display severe multifocal inflammatory responses, also involving the intestine, associated with an excessive inflammatory cytokines production by numerous cell types, including T cells (Shull M. M. et al., 1992; Christ M. et al. 1994).

Similarly, inhibition of TGF-β1 signalling in mouse by expressing a dominant negative mutant form of the TGF-γ1 receptor RII, results in an enhanced susceptibility to develop experimental colitis (Hahm K. B. et al., 2001).

Finally, it was shown that specific inhibition of TGF-β1 signaling in T cells by the expression of a dominant negative TGF-β receptor type II causes an autoimmune disease characterised by severe inflammatory infiltrations in lung and colon and the presence of circulating autoimmune antibodies (Gorelik L. at al., 2000). These data indicate that the loss of activity of a single anti-inflammatory molecule could be sufficient to alter intestinal homeostasis and to allow immune responses leading to tissutal damage.

TGF-β1 anti-inflammatory activity starts with the interaction of the molecule with a complex of heterodimeric transmembrane serine/threonine kinases receptors consisting of two subunits, named TGF-β1 R1 and TGF-β1 R2 respectively. Upon TGF-β1 binding, the receptors rotate relatively within the above mentioned complex, resulting in a trans-phosphorylation process and subsequent activation of TGF-β1 R1 by the constitutively active TGF-β1 R2 and capable of autophosphorylation.

The propagation of the TGF-β1-triggered signal to the nucleus is mediated by proteins belonging to the Smad family. Activated TGF-β1 R1 directly phosphorylates Smad2 and Smad3 proteins, which become able to interact with Smad4, thus enabling the complex Smad2-3/Smad4 to translocate to the nucleus, where it participates to the transcriptional control of some genes (Heldin C-H. et al., 1997).

The role of Smad3 in the TGF-β1 anti-inflammatory activity was supported by studies in animal models, which show that the deletion of the encoding gene for Smad3 is associated with diminished cell responsiveness to TGF-β1, and with a related development of inflammatory disease characterized by a massive infiltration of T-cells and pyogenic abscesses formation at gastrointestinal level (Yang X. et al., 1999).

Also other intracellular proteins, for example Smad7, belong to the Smads protein family. Such protein occupying TGF-β1 R1 interferes with the binding of Smad2/Smad3 to the receptor, thus preventing the phosphorylation and the activation. Hence, an increased expression of Smad7 protein is associated with an inhibition of the TGF-β1-mediated signaling (Hayashi H. et al., 1997).

The evaluation of the TGF-β1 expression in intestinal mucosa from IBD patients shows that said molecule production is paradoxically enhanced in comparison to what can be proved in the gut of normal patients (Lawrance I C. et al., 2001).

In a recent article the author of the present invention shows that mucosal samples from IBD patients are characterized by high levels of Smad7 and by reduced levels of active Smad3, thus indicating that during IBD the mechanism of TGF-β1-mediated signaling is compromised. The author of the present invention further showed that selective Smad7 abrogation by a specific antisense oligonucleotide 5'-GTCGCCCCTTCTCCCCGCAGC-3' (SEQ ID No 1) restores lamina propria mononuclear cells (LPMC) responsiveness to TGF-β1, resulting in a down-regulation of pro-inflammatory cytokine production, such as for example, TNF-α.

Moreover, also ex vivo experiments carried out on intestinal mucosa samples from IBD patients showed that administration of Smad7 antisense ODN restores TGF-β1 signaling mechanism and allows a diminished cytokine production (Monteleone et al., 2001).

During IBD, intestinal mucosa is infiltrated with an high number of T cells. These cells are regarded to be the main mediators of tissutal damage acting in such diseases.

The increased number of T cells in the intestinal mucosa from IBD patients is partly dependent on the resistance of such cells against stimuli inducing their death (apoptosis).

It is believed that the block of T cells apoptosis plays a key role in maintaining the mucosal inflammatory response in IBD (Boirivant et al., 1999). Indeed, enhancing T cell death associates with a resolution of the intestinal inflammation. The exact mechanism underlying the resistance of T cells against apoptosis during IBD is not yet known, even if locally released cytokines seem to be involved.

Data from cell-culture in vitro experiments and in vivo studies indicate that TGF-β1 can either prevent or trigger T cell death and that the capacity of the factor to mediate both responses is site-specific (Han S H. et al., 1998; Arsura M. et al., 1996)

Smad3 knockout mice exhibit a massive increase in the number of inflammatory cells at the intestinal level, thus suggesting a role for TGF-β1 in controlling intestinal T cell apoptosis at intestinal level (Yang et al., 1999).

Therefore Smad7 inhibition by the use of Smad7 synthetic antisense ODN may represent a novel and acceptable "endogenous" biotherapeutic approach to chronic inflammatory diseases, in particular to IBD, since, as above mentioned, it restores T cells responsiveness to TGF-β1.

Antisense oligonucleotides (ODN) are short synthetic oligonucleotidic sequences complementary to the messenger RNA (m-RNA) which encodes for the target protein of the specific and aimed inhibition. Such sequences, hybridizing to the m-RNA, make a double-strand hybrid trait, and this leads to the activation of ubiquitary catalytic enzymes, such as RNases H, which degrade DNA/RNA hybrid strands that develop in nature to trigger DNA duplication, thus preventing protein translation.

The selection of the most suitable m-RNA regions and sequences to hybridize to the ODN has empirical characteristics even if ODN complementary to the transcriptional initiation region 5' and to the splicing regions usually result more effective. The design of a remarkable number of antisense ODN, after identifying possible target sites, does not raise difficulties, thanks to the recent and advanced automated synthesis technologies owned by specialized companies in such field.

On the contrary the identification of the more active ODN, for possible therapeutic applications, requires a long-term screening work through efficacy assays in quantitative test. In relation to the above, antisense ODN sequences against specific target, among which Smad7, are already known (U.S. Pat. No. 6,159,697; assignee ISIS Pharmaceuticals Inc.).

The use of antisense ODN both for in vitro and in vivo gene regulation is thwarted by some problems, such as, the difficulty to pass through cellular membranes, due to the polianionic and then hydrophilic nature of these molecules, and the rapid enzymatic degradation.

To overcome these obstacles it is necessary to resort to chemical modification of the antisense ODN, such as, for example, phosphorothioation, as in the case of the above mentioned Smad7 specific sequence (Monteleone et al., 2001), or phosphoroamidation, that are substitutions of sulphur or nitrogen atoms in place of those oxygen atoms which are not the bridge atoms of the phosphodiester linkage.

As well as many biotechnological products, the demonstration of a biological activity points out a potential therapeutic activity.

Indeed ODN can be used either in the studies of both gene and protein functions involved in the pathogenesis of different diseases or for therapeutic purpose. Whereas in the former application field the antisense methodology was successful for the easiness of the guide principles, the shift from in vitro to in vivo experimentation is more complex, especially as regards pharmacokinetic, pharmacodynamic and toxicological aspects of these new drugs (Maggi A., 1998).

For example the Smad7 antisense ODN used in the previous experiments carried out by the author of the present invention (SEQ ID No 1), which shows in vitro biological activity, could show an increased risk of undesirable effects in vivo. In fact, such ODN contains two nucleotidic CG pairs which become CpG after phosporothioation, an essential process to enhance ODN stability. The latter are sequences endowed with a powerful stimulating activity of the immune system, therefore the use of the above mentioned ODN as such could made worse the course of any immunologic disease, Crohn's disease and ulcerative colitis included.

A similar therapeutic approach could not be hypothesized, especially in the case of Crohn's disease, a pathology mediated by a particular class of T lymphocytes, named Th1, under the interleukin 12 stimulus. Indeed CpG molecules, as powerful inductors of the IL-12 synthesis, could induce a further development of Th1 cells.

In addition, in vivo administration of the antisense ODN containing CpG dinucleotides is accompanied by an increased risk of side effects, in comparison to oligonucleotides without CpG. In particular, it has been proved an increased risk of hyperplasia of the reticuloendothelial system of the spleen, kidney and liver, as well as an increased proliferation of hematopoietic cells (Agrawal S. at al., 2002).

Another problem in the use of ODN is bound to the side effects resulting from the action of the metabolites derived from the degradation of the molecule, which results quite susceptible to nuclease attack, since it is not protected at the 5' and 3' ends.

Therein the necessity of chemical modification of the phosphorothioate antisense ODN backbone to CpG pairs and to 5' and 3' ends. Nevertheless the above said modifications of the ODN sequence could lead up to the reduction or the loss of the biological activity of inhibition of Smad7 synthesis and, sometimes, even to the inversion of the desired activity both in vitro and in vivo.

Likewise it may be important to dispose of experimental IBD models suitable for in vivo studies, which allow to enlarge the knowledge on the mechanisms involving the loss of the regulation of the immunitary response and their role in the onset of IBD pathology and on the possibility to modulate or prevent such response, thus limiting inflammation progression at mucosal level. In relation to the above the TNBS-mediated colitis represents a spread and valid model of mucosal inflammation which shows striking immunomorphological similarities with human CD (Neurath M. et al., 2000).

In the light of the above, it would be desirable to dispose of new therapeutic biological agents, like Smad7 antisense ODN, which are active both in vitro and in vivo, for the treatment of IBD through an "endogenous" biotherapeutic approach".

The author of the present invention has now found suitably modified antisense ODN sequences which exhibit an higher in vivo biological activity of inhibition of Smad7 expression in experimental models of IBD in comparison to their in vitro inhibitory activity, and also higher than that of other known sequences showing the same modifications and tested on the same models.

In particular, the ODN sequences which exhibit an higher in vivo biological activity were designed according to the phosphorothioate antisense ODN sequence SEQ ID No 1 targeting the site 403 of the human Smad7 RNA, used by the author of the present invention in the course of previous experiments.

In view of the potential and future use of such Smad7 phosphorothioate antisense ODN for the treatment of human pathologies said sequence was modified at CpG dinucleotides therein contained, hereinafter indicated as XY, because of their already mentioned immunogenicity.

The study carried out by the author has allowed to test in vivo and in vitro efficacy of different known and novel Smad7 antisense ODN and their possible toxicity, and to investigate if blocking Smad7 expression results in a resolution of mucosal inflammation in experimental models of IBD.

The above mentioned suitably modified antisense ODN sequences according to the present invention, in addition to an higher biological activity in vivo, showed a surprisingly absence of side effects in animals, in spite of what happens after the administration of other sequences during the course of the same study. Further, ODN sequences according to the invention showed their efficacy to limit lymphocytic infiltration and the ulterior inflammation propagation, that is an evidence not found for the other antisense ODN sequences herein tested.

The role of Smad7 as biological target clearly appears from these studies in experimental models, together with the possible therapeutic effects of its inhibition.

Furthermore, within the context of the present invention, another role of Smad7 on the induction of T cell apoptosis during IBD has been found. In fact, through the use of some Smad7 antisense ODN, it has been showed that TGF-β1 regulates intestinal T cell apoptosis and that a defective factor activity accounts for cell-resistance to apoptotic stimuli, which are responsible for maintaining the mucosal inflammatory response.

Therefore the objects of the present invention are Smad7 phosphorothioate antisense oligonucleotides up to 21 nucleotides in length which comprise a portion of at least 10 nucleotides of the following sequence (SEQ ID No 2):

5'-GTXYCCCCTTCTCCCXYCAG-3' wherein X is a nucleotide comprising a nitrogenous base selected from the group consisting of cytosine, 5-methylcytosine and 2'-O-methylcytosine and wherein Y is a nucleotide comprising a nitrogenous base selected from the group consisting of guanine, 5-methylguanine e 2'-O-methylguanine, provided that at least one of the nucleotides X or Y comprises a methylated nitrogenous base;

or the complementary sequence thereto.

Other objects of the present invention are the oligonucleotidic sequences of the different antisense oligonucleotide stereoisomers, such as diastereoisomers and enantiomers, as to the phosphor atoms of the internucleosidic linkage included in the sequence. Indeed the internucleosidic linkage can be phosphorothioate or methylphosonate and in both cases the phosphor bound to four different chemical groups represents a chiral centre.

Antisense oligonucleotides according to the present invention can have at least one methylphosphonate nucleotide into the sequence, which is placed, for example, either at only one of the 5' or 3' ends or at both 5' and 3' ends or along the oligonucleotidic sequence.

In a preferred embodiment the methylphosphonate nucleotide can be either X or Y, in such a way that internucleosidic linkage is the linkage between said nucleotides.

Further modifications can be carried out to the 5' and 3' ends and/or along the sequence of the antisense ODN to increase the stability of the molecule thus preventing the degradation by nucleases and reducing the risk of undesirable effects derived from the metabolite actions.

Antisense oligonucleotides according to the present invention can have further at least one nucleotide of the sequence which is a 2'-O-methylribonucleotide 5'-monophosphate, which is placed, for example, either at only one of the 5' or 3' ends or at both 5' and 3' ends or along the oligonucleotidic sequence.

Further objects of the present invention are the above, said antisense oligonucleotide wherein 2'-deoxyribonucleotides are replaced by ribonucleotides and 2'-deoxythymidine is replaced by uridine in such a way that antisense deoxyribonucleotidic sequences turn to the correspondent antisense ribonucleotidic sequences.

A preferred embodiment of the present invention is represented by antisense oligonucleotides having the sequence (SEQ ID No 3):

5'-GTXGCCCCTTCTCCCXGCAG-3' wherein X is 5-methyl 2'-deoxycytidine 5'-monophosphate. In a particular preferred embodiment, the invention relates to the above sequence further having a cytosine nucleotide at 3' end (SEQ ID No 16; 5'-GTXGCCCCTTCTCCCXGCAGC-3').

Another preferred embodiment is represented by antisense oligonucleotides having the sequence (SEQ ID No 4):

5'-ZTXGCCCCTTCTCCCXGCAZ-3'
wherein X is 5-methyl 2'-deoxycitidine 5'-monophosphate and Z is 2'-deoxyguanosine methylphosphonate.

According to another aspect, a preferred embodiment of the present invention is antisense oligonucleotide having the sequence (SEQ ID No 15):

5'-ZTXGCCCCTTCTCCCXGCAZC-3'
wherein X is 5-methyl 2'-deoxycytidine 5'-monophosphate and Z is 2'-deoxyguanosine methylphosphonate.

Antisense ODN sequences according to the present invention can be advantageously used in medical field; therefore further objects of the present invention are pharmaceutical compositions which comprise at least one of the above disclosed antisense oligonucleotides as active principle together with one or more pharmaceutically acceptable adjuvants and/or excipients, which are known to skilled person in this field.

Further the invention relates to the use of the aforesaid antisense oligonucleotide sequences for the preparation of a medicament for the treatment of the pathologies associated with Smad7 expression. In particular, such pathologies associated with Smad7 expression are IBD, such as, for example, CD and UC.

The present invention is now described, for illustrative but not limitative purposes, according to its preferred embodiments, with particular reference to the figures of the enclosed drawings, wherein.

Figure 6:
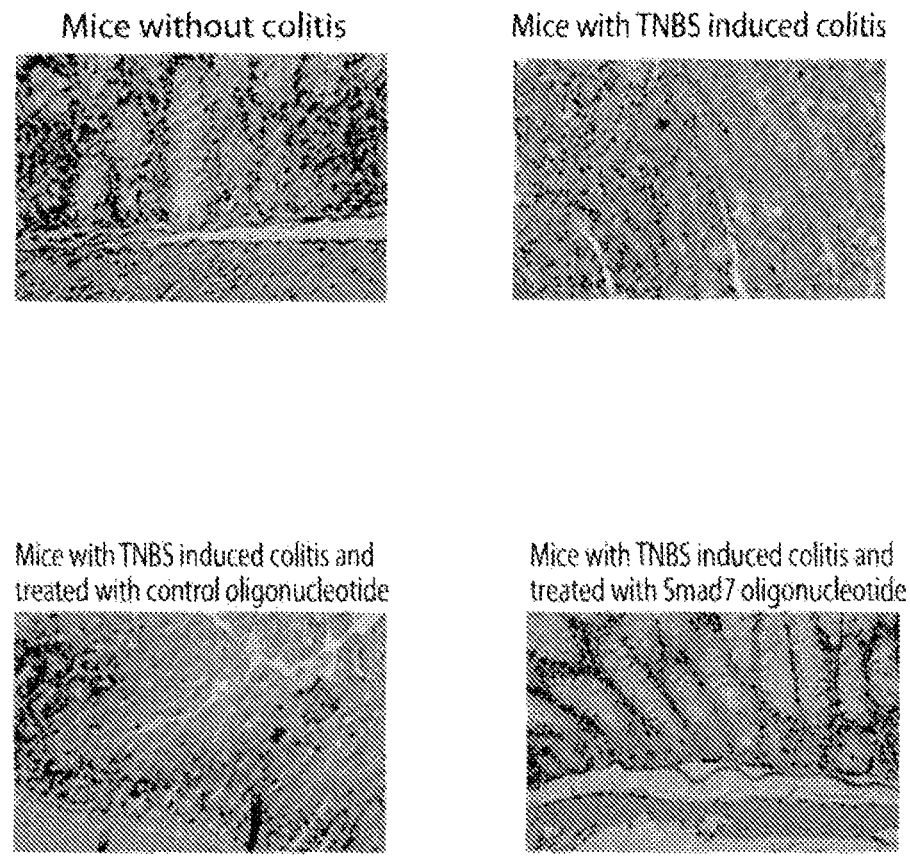
Figure 7:
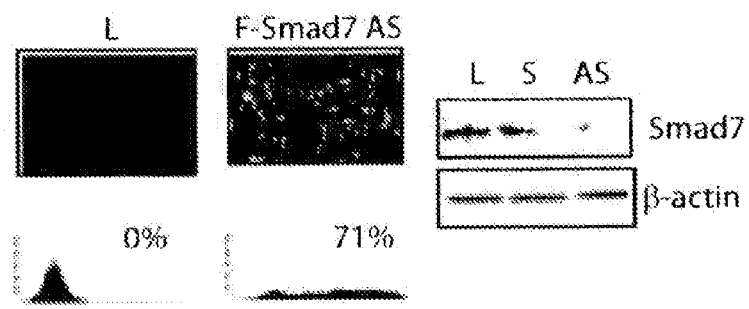
Figure 7:
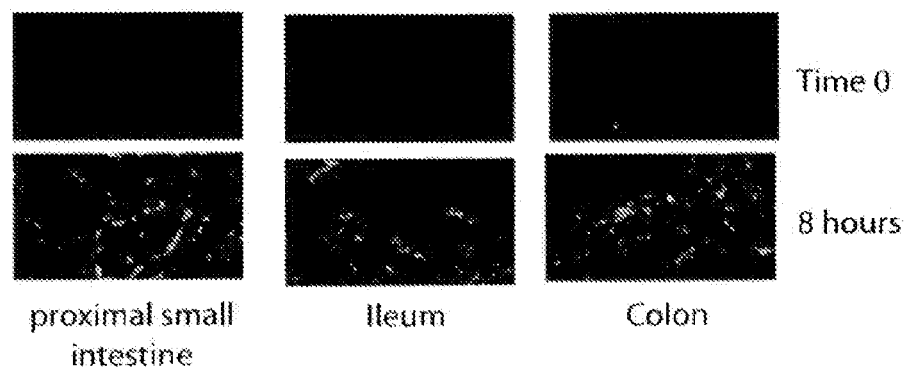
Figure 7:
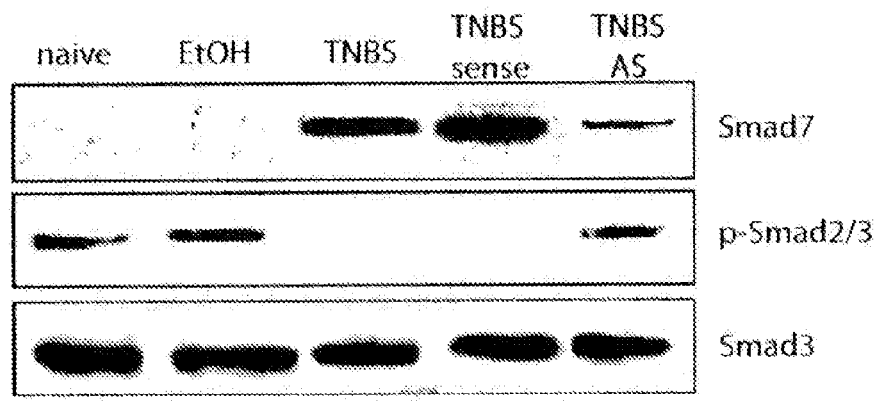
Figure 8:
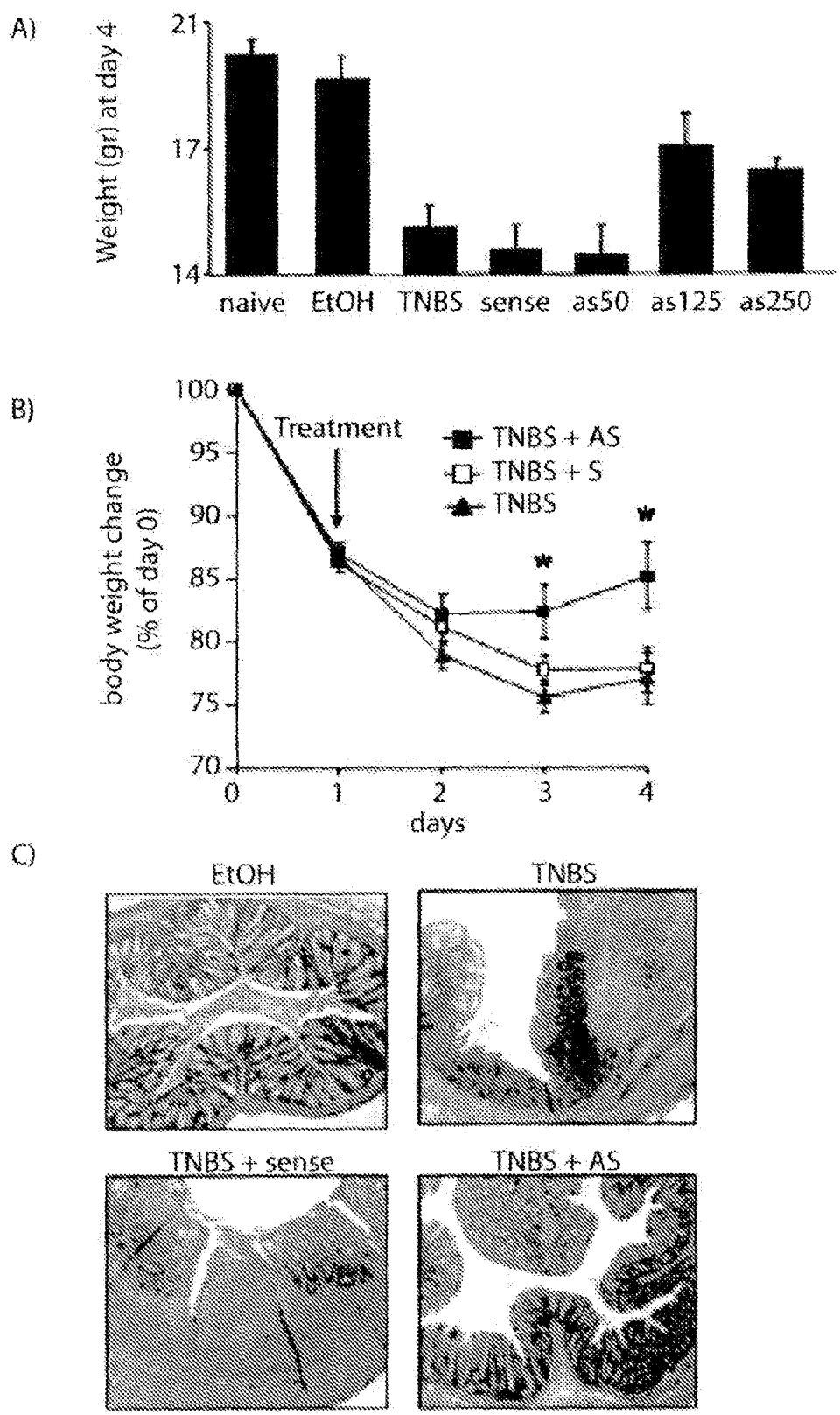
Figure 9:
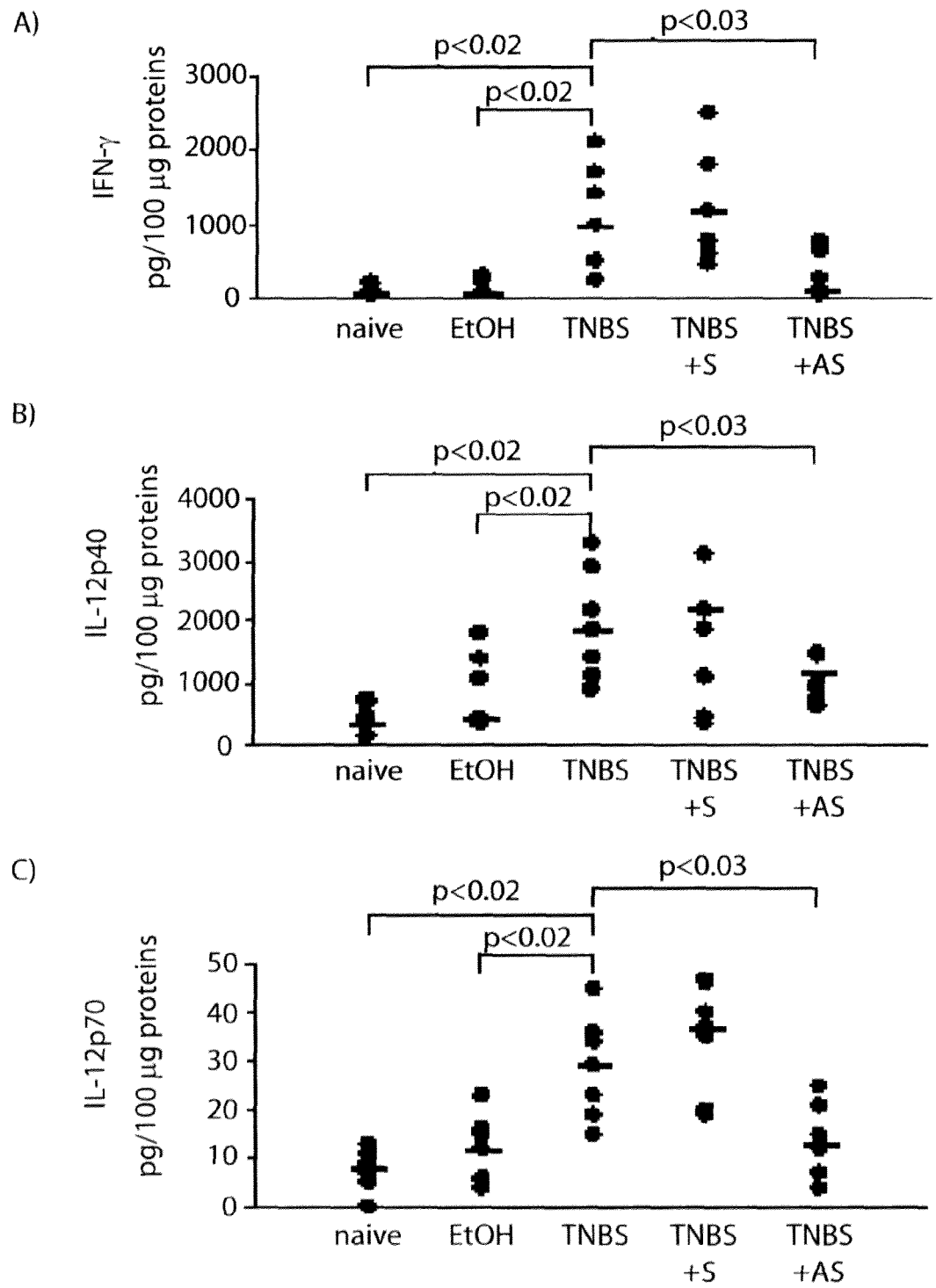
Figure 10:
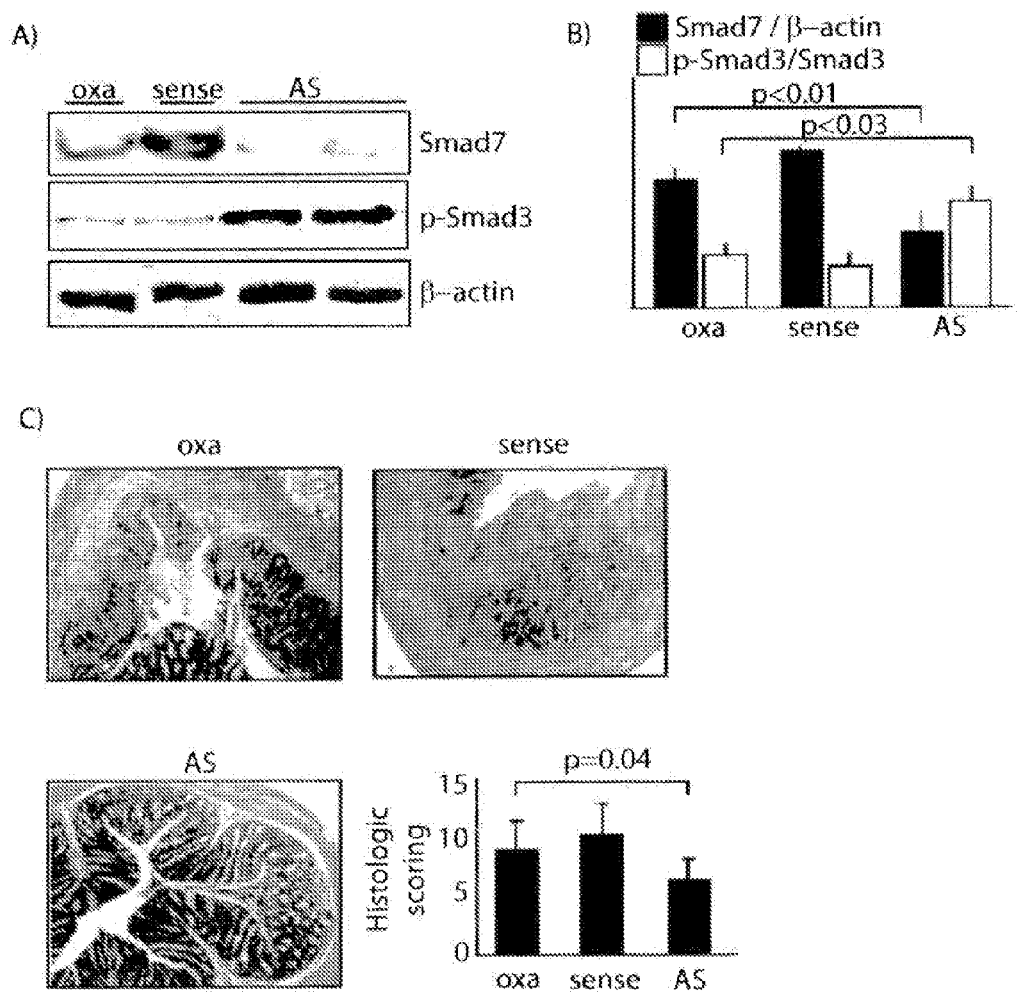
Figure 11:
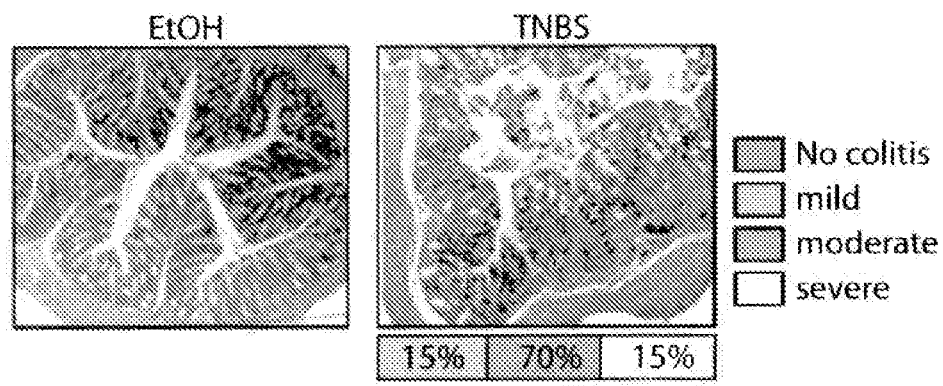
Figure 11:
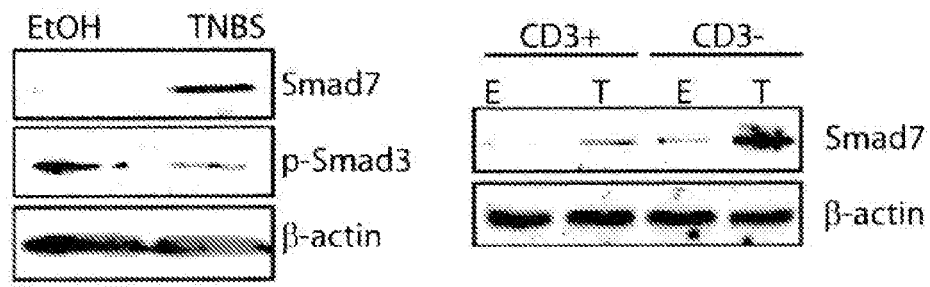
Figure 11:
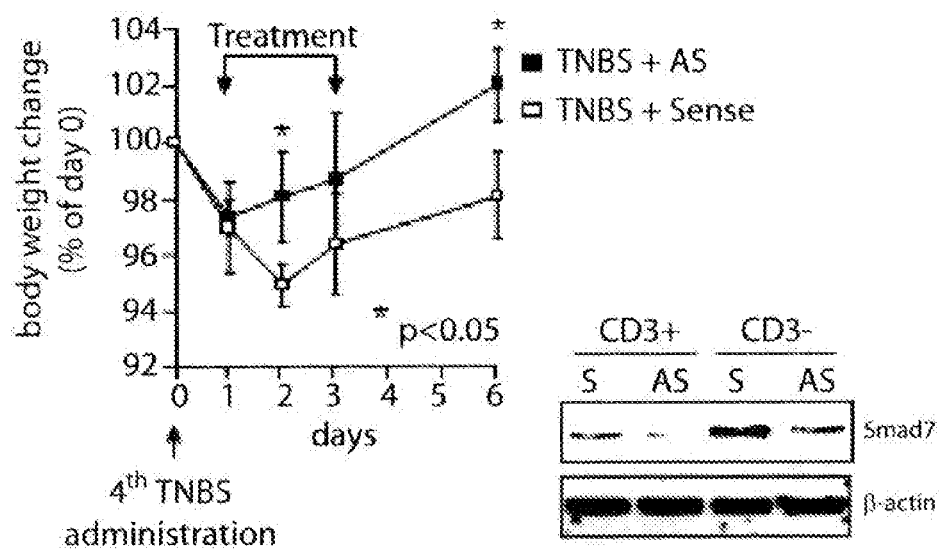

FIG. 6 shows histological aspect of a colon section from mice without colitis or with TNBS-induced colitis treated or not with Smad7 antisense oligonucleotide (SEQ. ID No 15) or with a control (sense); the figure is representative of three separate experiments wherein fourteen mice for each group have been studied. Magnification 40×;

FIG. 7, panel A, shows the inhibition of murine Smad7 protein by a specific antisense oligonucleotide. Transfection of RAW cells with a fluorescent (F)-labelled Smad7 antisense oligonucleotide was confirmed by microscopy (upper panel) and flow cytometry (lower panel) (numbers indicate the % of transfected cells). Right inset shows the inhibition of Smad7 protein by Smad7 antisense (AS) but not sense (S) oligonucleotide after 48 hours of culture. Cells were starved overnight and then transfected with the oligonucleotides in the presence of lipofectamine (L). Smad7 was assessed by Western blotting using total proteins. Panel B shows orally administered fluorescent-labelled Smad7 antisense oligonucleotide in mice with TNBS-colitis is taken up by both epithelial and lamina propria mononuclear cells in the proximal small intestine, terminal ileum and colon after 8 hours of administration. No staining is seen in mice with TNBS-colitis at time 0. Panel C shows representative Western blots showing down-regulation of Smad7 and enhanced p-Smad3 in the colon of mice with TNBS-colitis and treated with Smad7 antisense (AS) oligonucleotide. Mice with TNBS-colitis were orally administered with 125 µg/mouse of either AS or sense oligonucleotide at day 1, killed at day 4, and total extracts used for Smad analysis. One of 6 representative experiments analysing in total 12 mice per group is shown;

FIG. 8, panel A, shows the effects of different doses of orally administered Smad7 antisense (AS) oligonucleotide on weight of mice with TNBS colitis. Mice were left untreated (naïve) or treated with TNBS, and 1 day after the induction of colitis administered or not with Smad7 sense (125 µg/mouse) or AS (50, 125 or 250 µg/mouse). Data indicate the cumulative mean weight data from 2 separate experiments. In each experiment, each group consisted of at least four mice. Bars represent S.E.M. Panel B shows weight changes of mice with TNBS-colitis after a single administration of Smad7 AS or sense oligonucleotide. Either the AS or sense oligonucleotide (125 µg/mouse) was orally administered 1 day after (day 1) the induction of colitis, and weight of each mouse was then daily recorded. Each point represents the cumulative mean weight data from 4 separate experiments. In each experiment, each group consisted of at least four mice. Bars represent S.E.M. Panel C shows histologic evaluation of TNBS-colitis in mice treated or not with Smad7 antisense (AS) or sense oligonucleotide. Photomicrograph (×20) of an H&E-stained paraffin section of a representative colon from mice belonging to each group. Severe mucosal mononuclear cell infiltrate and disruption of the normal crypt architecture with epithelial ulceration and loss of goblet cells is evident in the colon of mice with TNBS either left untreated or treated with the sense oligonucleotide. In contrast, only small scattered areas of cellular infiltration is seen in the colon of mice treated with the Smad7 AS oligonucleotide. The photomicrographs are representative of 3 separate experiments in which at least 4 mice per group were studied;

FIG. 9, shows the inhibition of Smad7 protein by a Smad7 antisense (AS) oligonucleotide in mice with TNBS-colitis results in decreased tissue expression of IFN-γ(A), IL-12 (both p40 and p70, panels B and C). One day after the TNBS-colitis induction, mice were either left untreated or treated with 125 µg/mouse of Smad7 AS or sense oligonucleotide. Mice were then sacrificed at day 4, and colonic samples used for extracting total proteins. Cytokines were analyzed by ELISA and data are expressed as pg/µg total proteins. Each point represents the value of cytokine in colonic samples taken from a single mouse. Horizontal bars indicate the median value. Induction of TNBS-colitis results in a significant increase in the production of IFN-γ in comparison to naive and ethanol (EtOH)-treated mice. Consistently, both IL-12/p40 and IL-12/p70 are increased during TNBS-colitis in comparison to control mice. Oral administration of Smad7 antisense but not sense oligonucleotide to mice with TNBS-colitis reduces IFN-γ as well as IL-12/P40 and IL-12/p70 synthesis;

FIG. 10, panel A, shows representative Western blots showing both down-regulation of Smad7 and enhanced p-Smad3 in mice with oxazolone (oxa)-colitis and treated with Smad7 antisense (AS) or sense oligonucleotide. Mice were orally administered with 125 µg/mouse of either AS or sense oligonucleotide the day after the induction of colitis (day 1), then killed at day 3, and total proteins extracted from the colon and used for Smad analysis. One of 3 representative experiments analysing in total 7 mice per group is shown. B. Quantitative data of either Smad7/β-actin or p-Smad3/Smad3 as measured by densitometry scanning of Western blots. Values are expressed in arbitrary units (a.u.) and indicate mean±S.E.M. of all experiments. Panel C shows the histologic analysis of the colons from mice with oxazolone-induced colitis, either left untreated or treated with Smad7 antisense (AS) or sense oligonucleotide. Photomicrographs of H&E-stained paraffin section of distal colon (×20) from mice at day 3 after the induction of colitis are shown. A severe transmural inflammation with bowel wall thickening, epithelial cell ulceration and loss of goblet cells are seen in the colon of mice with oxazolone-colitis either left untreated or treated with the sense oligonucleotide. In contrast, a minimal mononuclear cell infiltration of the lamina propria with maintenance of the epithelial cell architecture is present in the colon of mice treated with the Smad7 AS oligonucleotide. Right inset shows the histological score of colonic sections from mice with oxa-induced colitis, either left untreated or treated with Smad7 antisense (AS) or sense oligonucleotide. Data indicate the mean±SD of 2 separate experiments analysing in total 7 mice per each group. Treatment of mice with Smad7 AS but not sense significantly reduces the colonic inflammation;

FIG. 11, panel A, shows photomicrograph (×20) of an H&E-stained paraffin section of a representative colon of 2 mice (1 naïve and 1 with TNBS-induced colitis). Severe mucosal mononuclear cell infiltration and disruption of the normal crypt architecture with epithelial ulceration and loss of goblet cells is evident in the mouse with relapsing TNBS-colitis. In this experiment, mice were sacrificed one day after the last TNBS injection. Percent of animals harboring mild, moderate, and severe colitis are shown as bar graphs. Panel B shows enhanced Smad7 and decreased p-Smad3 expression in mice with relapsing colitis. The day after the last (fourth week) TNBS injection mice were killed, and colonic total proteins analysed for Smad molecules by Western blotting. Right inset. High Smad7 is seen in purified lamina propria T lymphocytes (CD3+) and CD3-negative LPMC from mice with relapsing TNBS (T)-colitis in comparison to ethanol (E)-treated mice. Cells were isolated from the colon of 3 mice per each group. Panel C shows oral administration of Smad7 antisense (AS) oligonucleotide leads to an early recover in weight in mice with TNBS-induced chronic colitis. Colitis was induced as indicated in material and methods and the day after the last TNBS injection mice were allocated to receive either Smad7 AS or sense oligonucleotide. Weight changes were then daily recorded. Each point represents the cumulative mean weight data from two experiments in which 8 mice per group were considered. Bars represent S.E.M. Right inset. Administration of Smad7 antisense to mice with relapsing TNBS-colitis reduces Smad7 expression both in colonic CD3-positive and CD3-negative LPMC. Cells were isolated from the colon of 3 mice per each group. Panel D shows histologic evaluation of chronic TNBS-colitis in mice treated with Smad7 antisense (AS) or sense oligonucleotide. Photomicrograph (×20) of an H&E-stained paraffin section of a representative colon from mice belonging to each group. A moderate mucosal mononuclear cell infiltration, dilatation of the colon, and hyperplastic lymphoid follicles are seen in sections from mice treated with sense oligonucleotide, whereas only a minimal inflammatory infiltrate is noted in the colon of mice treated with the Smad7 AS. The photomicrographs are representative of experiments in which 5 mice per group were studied. Percent of animals with no evidence of colitis or harboring mild, moderate, and severe inflammation are shown as bar graphs.

EXAMPLE 1

Study on the Effect of Smad7 Antisense Oligonucleotides According to the Present Invention on Intestinal T Cells Apoptosis Materials and Methods
Synthesis of Antisense ODN All the Smad7 antisense ODN were synthesized by MWG Biotech AG (MWG Biotech S.r.l., Florence) employing standard automated techniques with an automated DNA synthesizer using standard phosphoroamidite chemistry protocols (Lesiak K. et al., 1993; Xiao W. et al., 1996).

Oligonucleotides containing 5-methyl-2'-deoxycitidine (5-Me-dC) were synthesized according to known synthesis methods (Sanghvi et al., 1993) using commercially available phosphoroamidites, whereas synthesis of modified oligonucleotides containing methylphosphonate groups (MeP) was accomplished using known protocols (Maier M A. et al., 2002).

The purification of the oligonucleotidic molecules has been carried out HPSF technology, developed by MWG Biotech. Such purification method has revealed an high efficiency since it allows removing failure sequences synthesized during the automated chemical synthesis process, such as, for example, n-1, n-2, n-x sequences, that standard purification classic methods are not capable to remove.

The above mentioned technology, besides enabling to obtain 100% of the desired length sequences without undesirable failure products, allows avoiding next desalting operation, since the purified sequences are free of both salt and metal ions.

Given the absence of any salt, oligonucleotides were eventually analysized by MALDI-TOF mass spectrometry techniques according to standard protocols (Guerlavais T. et al., 2002; Ragas J A. et al., 2000). Then oligonucleotides were sterilized and the resulting solution was quantified as optical density (OD) by UV/visible spectrophotometer. Finally the molecules were resuspended in sterile PBS1× before using.

All the used antisense ODN target Smad7 m-RNA sites which have 100% homology between human and mouse. In all the following oligonucleotides the internucleoside linkage is a phosphorothioate linkage.

The antisense ODN sequences being used in the present study have been designed according to the phosphorothioate antisense ODN sequence 5'-GTCGCCCCTTCTC-CCCGCAGC-3' (SEQ ID No 1) targeting the site 403 of the human Smad7 m-RNA, used by the author of the present invention in the course of previous experiments (Monteleone et al., 2001).

The Smad7 antisense ODN sequence 5'-MePGTMe-dCGCCCCTTCTCCCMe-dCGCAMePG-3' (SEQ ID No 4) targets the site 403 of the human Smad7 m-RNA. This is a mixed-backbone oligonucleotide wherein the cytosine belonging to CpG pairs of SEQ ID No 1 were replaced by 5-methylcytosine (herein indicated as Me-dC). In addition, methylphosphonate linkages were placed at the ends of the molecule (herein indicated as MeP).

The Smad7 antisense ODN sequence 5'-GTTTGGTCCT-GAACATGC-3' (SEQ ID No 5) targets the site 294 of the human Smad7 m-RNA.

Mucosal samples were taken from resection specimens of 6 patients with moderate-to-severe CD and 4 patients with severe UC. In addition, intestinal mucosal samples were taken from 10 unaffected IBD patients undergoing colectomy for colon carcinoma (ethical approval was obtained by local committee). LPMC were prepared using the DTT-EDTA-collagenase procedure and resuspended in RPMI 1640 (Sigma-Aldrich S.r.l., Milan) supplemented with a serum replacement reagent HL-1 (Biowhittaker, Wokingham, UK).

Cells were cultured in the presence and absence of TGF-β1 (Sigma-Aldrich, final concentration ranging from 1 to 5 ng/ml) and after 48 hours of incubation were analyzed for the level of apoptosis.

In other experiments, LPMC isolated from IBD patients intestine were resuspended in RPMI 1640 supplemented with HL-1 and cultured in the presence and absence of the above mentioned Smad7 antisense ODN (SEQ ID No 4, SEQ ID No 5), and in the presence of a control sense oligonucleotide (both used at a concentration of 2 µg/ml). After 24 hours, an aliquot of LPMC was used for extracting proteins and evaluate Smad7 expression. The remaining cells were extensively washed and resuspended in RPMI 1640 plus HL-1 and cultured in the presence or absence of TGF-β1 (5 ng/ml) for 48 hours and then analyzed for apoptosis.

Analysis of Apoptosis by Flow Cytometry

Apoptosis was analyzed by propidium iodide (PI) staining followed by flow cytometry.

Cells were washed, incubated for 15 minutes at 37° C. in 5 µl ribonuclease A (0.6 µg/ml, 30-60 Kunitz units, Sigma-Aldrich), and then chilled on ice. Propidium iodide (100 µg/ml) was added before analysis by flow cytometry.

T cells were identified using a specific monoclonal anti-CD3 antibody (DAKO Ltd., Cambridgeshire, UK).

Protein Extraction and Western Blot Analysis

LPMC were homogenized and total proteins were extracted in buffer A containing 10 mM Hepes (pH 7,9), 10 mM KCl, 0.1 mM EDTA and 0.2 mM EGTA. Buffer was supplemented with 1 mM dithiothreitol (DTT), 10 µg/ml aprotinin, 10 µg/ml leupeptin and 1 mM phenylmethanesulphonyl fluoride (all reagents from Sigma-Aldrich).

Smad7 protein was analyzed using a specific rabbit anti-human Smad7 antibody (1:400 final dilution, Santa Cruz Biotechnology, Inc., CA; USA). Goat anti-rabbit antibodies conjugated to horseradish peroxidase (Dako Ltd) were used at 1:20,000 final dilution to detect primary antibody binding and immunoreactivity was visualized with a chemiluminescence kit (Pierce, Rockford, Ill., USA).

Organ Culture

Mucosal explants taken from the surgical specimens of patients were cultured in the presence or absence of Smad7 antisense ODN (SEQ ID No 4, SEQ ID No 5; both used at a final concentration of 10 µg/ml) for 40 hours.

As negative control, a mucosal explant was cultured in the presence of Smad7 sense ODN.

At the end of the culture, mucosal explants were collected and used for analyzing the number of lamina propria T lymphocytes by immunohistochemistry.

For this purpose, mucosal sections were prepared and stained with a monoclonal anti-CD3 antibody (DAKO). Goat anti-mouse antibodies conjugated to alkaline phosphatase (DAKO) were used to detect primary antibody binding.

Results

The results obtained in the different experiments show how TGF-β1 enhanced, dose-dependently, apoptosis of T lymphocytes isolated from the intestine of normal subjects.

Table 1 shows the percentage of apoptotic T lymphocytes after 48 hours of culture. Numbers are the results of 4 separate experiments in which T cells isolated from the intestine of four normal subjects were used.

TABLE 1

|  | Exp. 1 | Exp. 2 | Exp. 3 | Exp. 4 |
|---|---|---|---|---|
| Unstimulated | 18% | 17% | 19% | 23% |
| TGF-β1 (0.2 ng/ml) | 22% | 24% | 23% | 25% |
| TGF-β1 (1 ng/ml) | 31% | 33% | 28% | 31% |
| TGF-β1 (5 ng/ml) | 33% | 34% | 32% | 37% |

In contrast, T lymphocytes isolated from four IBD patients showed a partial resistance to the TGF-β1-induced apoptosis signal as shown in the results reproduced in Table 2 which shows the percentage of apoptotic T lymphocytes after 48 hours of culture.

TABLE 2

|  | Exp. 1 | Exp. 2 | Exp. 3 | Exp. 4 |
|---|---|---|---|---|
| Unstimulated | 11% | 10% | 9% | 7% |
| TGF-β1 (0.2 ng/ml) | 12% | 9% | 8% | 5% |
| TGF-β1 (1 ng/ml) | 10% | 11% | 11% | 8% |
| TGF-β1 (5 ng/ml) | 16% | 13% | 14% | 15% |

In particular, from the analysis of data shown in Table 2 no meaningful increase in apoptosis was seen when T cells from IBD patients were cultured in the presence of either 0.2 ng/ml or 1 ng/ml TGF-β1 concentration. In contrast, stimulation of T cells from IBD patients with 5 ng/ml TGF-β1 resulted in a small increase in apoptosis.

Treatment of T lymphocytes isolated from IBD patients with the Smad7 antisense ODN SEQ ID No 4 restored the cell responsiveness to TGF-β1, resulting in enhanced cell apoptosis, as shown in percentage values of T lymphocytes reproduced in Table 3. Data refer to four separate experiments in which T cells isolated from the intestine of four IBD patients, were cultured with medium alone (unstimulated) or pre-treated with medium and sense (control) or antisense oligonucleotides overnight and then stimulated with TGF-β1 (1 ng/ml).

TABLE 3

|  | Exp. 1 | Exp. 2 | Exp. 3 | Exp. 4 |
|---|---|---|---|---|
| Unstimulated | 10% | 9% | 8% | 7% |
| Medium | 11% | 9% | 8% | 5% |
| ODN Sense | 12% | 10% | 10% | 8% |
| ODN Antisense | 33% | 32% | 23% | 19% |

Figure 1:
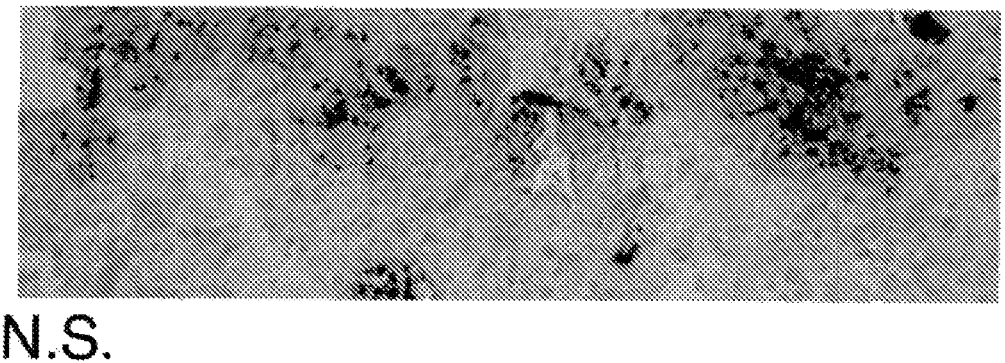
FIG. 1 shows the effect of Smad7 ODN antisense (5'-MePGTMe-dCGCCCCTTCTCCCMe-dCGCAMePG-3' (SEQ ID No 4) and sense on the presence of CD3+ T lymphocytes in ex vivo organ cultures of mucosal explants of CD patients after 40 hour treatment.
Figure 1:
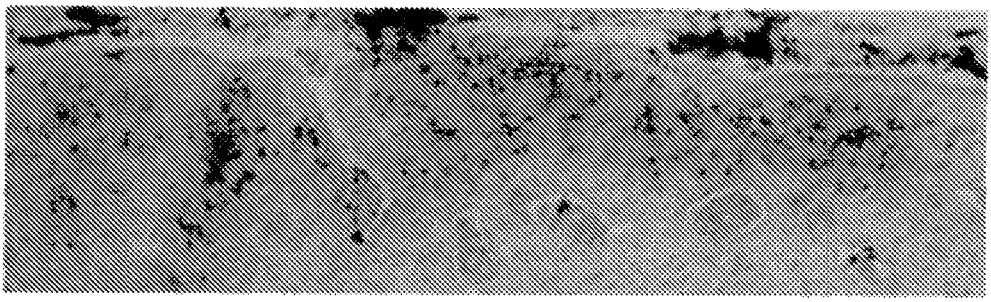
Figure 1:
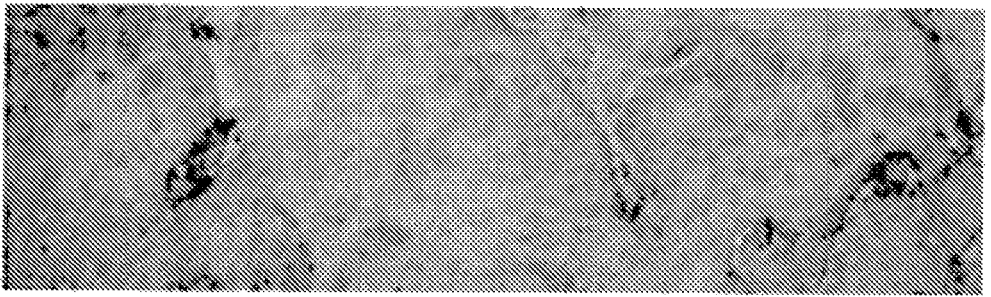

Furthermore, using ex vivo organ culture, the author of the present invention demonstrated that treatment of IBD biopsies with Smad7 antisense ODN according to the present invention significantly decreased the number of mucosal CD3+ T cells, as shown in the immunohistochemistry of FIG. 1. The latter shows that the treatment with the antisense ODN reduces the number of mucosal CD3+ T cells.

Together these observations suggest the possibility that high Smad7 level plays a crucial role in prolonging T cell survival, thereby contributing to the propagation of local inflammation in IBD.

Thus, blocking Smad7 could represent a promising strategy to control mucosal inflammation in these condition.

EXAMPLE 2

In Vivo and In Vitro Studies on the Effects of the Administration of Smad7 Antisense and Sense Oligonucleotides in Experimental Models of TNBS-Induced Colitis Material and Method All the Smad7 antisense and sense ODN were synthesized by MWG Biotech S.r.l. (Firenze) employing the standard techniques previously described.

The used antisense ODN target Smad7 m-RNA sites which have 100% homology between human and mouse. In all the following oligonucleotides the internucleoside linkage is a phosphorothioate linkage. All the following sequences were used in the experiments carried out on the experimental induced-colitis models.

The Smad7 antisense ODN SEQ ID No 1 (5'-GTCGC-CCCTTCTCCCCGCAGC-3') targets the site 403 of the human Smad7 m-RNA already used by the author of the present invention in the course of experiments published in a previous article (Monteleone et al., 2001).

For the further study concerning the role of Smad7 on the regulation of T cell apoptosis in LPMC isolated from the intestine of IBD patients the following antisense oligonucleotide sequences SEQ ID No 4 e SEQ ID No 5 were used.

The Smad7 antisense ODN sequence 5'-MePGTMe-dCGCCCCTTCTCCCMe-dCGCAMePG-3' (SEQ ID No 4) targets the site 403 of the human Smad7 m-RNA. This is a mixed-backbone oligonucleotide wherein the cytosine belonging to CpG pairs in the position 3 and 16 of SEQ ID No 1 were replaced by 5-methylcytosine (indicated as Me-dC). In addition, methylphosphonate linkages were placed at the ends of the molecule (indicated as MeP).

The Smad7 antisense ODN sequence 5'-GTTTGGTCCT-GAACATGC-3' (SEQ ID No 5) targets the site 294 of the human Smad7 m-RNA. The internucleoside linkages included therein are phosorothioate linkages.

The Smad7 antisense ODN sequence 5'-GTTTGGTCCT-GAACAT-3' (SEQ ID No 6) targets the site 296 of the human Smad7 m-RNA.

The Smad7 antisense ODN sequence 5'-GTTTGGTCCT-GAACATG-3' (SEQ ID No 7) targets the site 295 of the human Smad7 m-RNA.

The Smad7 antisense ODN sequence 5'-AGCAC-CGAGTGCGTGAGC-3' (SEQ ID No 8) targets the site 577 of the human Smad7 m-RNA.

The Smad7 antisense ODN sequence 5'-MePAGCAC-MedCGAGTGMedCGTGAGCMeP-3' (SEQ ID No 9) targets the site 577 of the human Smad7 m-RNA. This is a mixed-backbone oligonucleotide wherein the cytosine in the position 6 and 12 of SEQ ID No 8 were replaced by 5-methylcytosine. In addition, methylphosphonate linkages were placed at the ends of the molecule.

The Smad7 antisense ODN sequence 5'-CGAACAT-GACCTCCGCAC (SEQ ID No 10) targets the site 233 of the human Smad7 m-RNA.

The Smad7 antisense ODN sequence 5'-Me-d CGA ACA TGA CCT CMe-d CG CAC-3' (SEQ ID No 11) targets the site 233 of the human Smad7 m-RNA. This is a mixed-backbone oligonucleotide wherein the cytosine in the position 1 and 14 of SEQ ID No 10 were replaced by 5-methylcytosine.

The Smad7 antisense ODN sequence 5'-GTMe-dCGC-CCCTTCTCCCMe-dCGCAG-3' (SEQ ID No 12) targets the site 403 of the human Smad7 m-RNA. This is a mixed-backbone oligonucleotide wherein the cytosine belonging to CpG pairs in the position 3 and 16 of SEQ ID No 1 were replaced by 5-methylcytosine (indicated as Me-dC).

The Smad7 antisense ODN sequence 5'-GATCGTTTG-GTCCTGAA-3' (SEQ ID No 13) targets the site 299 of the human Smad7 m-RNA.

The Smad7 antisense ODN sequence 5'-ATCGTTTG-GTCCTGAAC-3' (SEQ ID No 14) targets the site 298 of the human Smad7 m-RNA.

The Smad7 antisense ODN sequence MePGTMe-dCGC-CCCTTCTCCCMe-dCGCAMePGC (SEQ ID No 15) targets the site 403 of the human Smad7 m-RNA. This is a mixed-backbone oligonucleotide wherein the cytosine belonging to CpG pairs in the position 3 and 16 of SEQ ID No 1 were replaced by 5-methylcytosine (indicated as Me-dC). In addition, methylphosphonate linkages were placed at one of the ends of the oligonucleotides and at the guanine residue in position 20.

Induction of Colitis

Five to six-week old male SJL/J mice were maintained in a specific pathogen-free animal facility. For induction of colitis, 2.5 mg TNBS (pH 1.5-2.0; Sigma Aldrich) in 50% ethanol was administered per rectum to lightly anesthetized mice through a 3.5 F catheter. The catheter tip was inserted 4 cm proximal to the anal verge, then 100 ml of fluid (TNBS/ethanol) was slowly instilled into the colon.

To ensure distribution of the TNBS within the entire colon and cecum, mice were held in a vertical position for 30 seconds after the injection. Some of the mice were administered with 50% ethanol alone using the same technique and were used as controls.

Histologic Assessment of Colitis

Tissues removed from mice at indicated times of death were fixed in 10% formalin solution (Sigma Aldrich), embedded in paraffin, cut into tissue sections and stained with hematossiline and eosine. Stained sections were examined for evidence of colitis using different criteria such as the presence of lymphocyte infiltration, elongation and/or distortion of crypts, frank ulceration and thickening of the bowel wall.

The degree of inflammation on microscopic cross-sections of the colon was graded from 0 to 4 as follows:

0: no evidence of inflammation;

1: low level of lymphocyte infiltration with infiltration seen in a <10% high-power field (hpf=high power field), no structural changes observed;

2: moderate lymphocyte infiltration with infiltration seen in <10-25% hpf, crypt elongation, bowel wall thickening which does not extend beyond mucosal layer;

3: high level of lymphocyte infiltration with infiltration seen in <25-50% hpf, thickening of bowel wall which extends beyond mucosal layer;

4: marked degree of lymphocyte infiltration with infiltration seen in >50% hpf, high vascular density, crypt elongation with distortion, transmural bowel wall-thickening with ulceration.

Isolation of Lamina Propria Mononuclear Cells (LPMC) and Treatment of Cells with Smad7 Antisense ODN The lamina propria mononuclear cells (LPMC) were isolated from colonic specimens. The specimens were first washed in HBSS-calcium magnesium free (Hanks' balanced salt solution, Sigma-Aldrich) and cut into 0.5-cm pieces. They were then incubated twice, each time for 15 minutes in HBSS containing EDTA (0.37 mg/ml) and dithiothreitol (0.145 mg/ml) at 37° C. The tissues were then digested in RPMI containing collagenase D (400 U/ml, Boehringer Mannheim Biochemicals, Indianapolis, Ind.) and DNase I (0.01 mg/ml, Boehringer Mannheim Biochemicals, Indianapolis, Ind.) in a shaking incubator at 37° C.

The LPMC released from the tissue were resuspended in 100% Percoll, layered under a 40% Percoll gradient (Pharmacia Biotech AB, Uppsala, Sweden), and spun at 1,800 rpm for 30 minutes to obtain the lymphocyte-enriched population.

To assess the in vitro efficacy of Smad7 antisense ODN, the LPMC isolated from TNBS-treated mice, were resuspended in RPMI 1640 (Sigma-Aldrich) supplemented with a serum replacement reagent HL-1 (Biowhittaker) at a final concentration of $1 \times 10^6$/ml in 24 well plates. For transfection of antisense ODN, 2 µl of lipofectamine 2000 reagent (LF, Invitrogen Italia SRL, San Giuliano Milanese) was used for each ml of cell medium following the protocol. Then, 2 µg/ml of antisense ODN and LF were combined and allowed to incubate for 20 minutes at room temperature. The obtained mixture was then added directly to the cells. After overnight culture, the cells were removed from the plate and used for analysis of Smad7 by Western blotting.

Treatment of Mice with Smad7 Antisense ODN

Two days after treatment with TNBS, mice were administered per rectum 150 µg of each Smad7 antisense or sense oligonucleotide. At least 5 mice for group were examined. At fifth day mice were sacrificed and whole intestinal mucosal samples were taken and analysed for Smad7 and Smad3 content by Western blotting. In addition intestinal mucosal inflammation degree entity was evaluated.

Protein Extraction and Western Blot Analysis

Both lamina propria mononuclear cells and whole colonic specimens were homogenized using the above procedure. Then Smad7 expression was revealed by Western blotting.

At the end, the blots were stripped using a commercially available solution (Pierce) and probed with anti-actin antibodies (Sigma-Aldrich) to verify the same amount of protein were filled in each well. Detection was accomplished using a chemiluminescence kit (Pierce). The intensity of bands was analysed by a densitometer.

Both LPMC and whole colonic specimen samples proteins were also analyzed for the content of phosphorylated and total Smad3 protein by Western blotting using specific commercially available antibodies (Santa Cruz).

For the analysis of phosphorylated Smad3 a specific rabbit anti-human antibody capable to recognize phosphorylated Smad2/3 proteins as antigen (1:500 final dilution), and a goat anti-rabbit antibody conjugated to horseradish peroxidase (1:20,000 dilution) were used. Immunoreactivity was visualized with a chemiluminescence kit (Pierce).

After detection, blots were stripped using a commercially available solution (Pierce) and incubated with a specific goat anti-human Smad3 antibody (1:500 final dilution) followed by a rabbit anti-goat antibody conjugated to horseradish peroxidase (1:20,000 dilution); then immunoreactivity was visualized with the above mentioned chemiluminescence kit (Pierce).

Test ELISA

The amount of active TGF-$\beta$1 was determined in the intestinal mucosal samples. To this aim total proteins were extracted from mucosal samples from mice with or without TNBS-induced colitis as above indicated. The levels of active TGF-$\beta$1 were analyzed using a commercially available ELISA kit (R&D Systems, Space Import-Export Srl, Milano). Optical density was measured on a Dynatech MR 5000 ELISA reader at a wavelength of 490 nm. Data were expressed as pg/100 µg of total proteins.

Results

After receiving TNBS mice developed diarrhoea and weight loss by evidence of the induction of colitis. The colon was macroscopically enlarged and histological analysis of its mucosa showed moderate to severe inflammatory lesions.

To examine if induction of TNBS-colitis was associated with changes in the production of TGF-$\beta$1, colonic specimens were taken from mice with or without colitis and analyzed for the content of active TGF-$\beta$1 by ELISA.

As several cell types which have the potential to synthesize TGF-$\beta$1 are present at intestinal level, it was evaluated in whole intestinal mucosal rather than LPMC samples.

Figure 2:
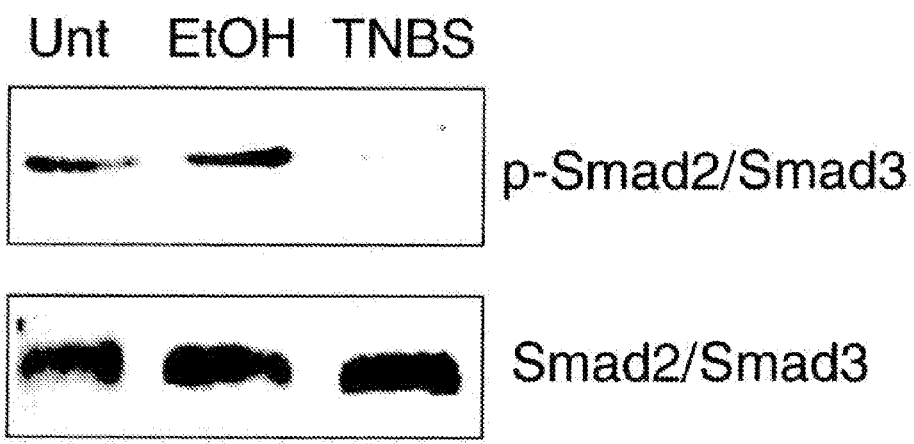
FIG. 2 shows the analysis of the expression of p-Smad2/Smad3 complex and of the total Smad2/Smad3 complex in LPMC isolated from the intestine of TNBS-treated mice (TNBS), untreated (Unt), treated with ethanol (EtOH) as controls.
Figure 3:
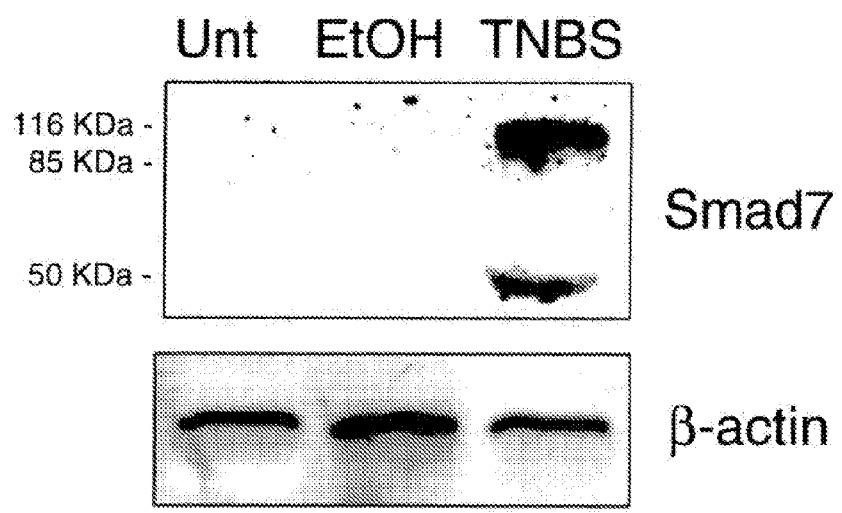
FIG. 3 shows the analysis of the Smad7 expression in LPMC isolated from the intestine of TNBS-treated mice (TNBS), untreated (Unt), treated with ethanol (EtOH) as controls.

In the absence of colitis low levels of active TGF-$\beta$1 were detected (85±12 and 94±26 pg/µg of total protein in unstimulated and controls mice respectively). Significantly enhanced TGF-$\beta$1 levels were measured in mucosal samples from mice with TNBS-induced colitis (985±120 pg/µg of total protein) ($p<0.01$). Even though this result seems to suggest that during TNBS-induced colitis there could be an increasing TGF-$\beta$1 activity, the analysis of intracellular levels of active Smad3 in intestinal LPMC isolated from mice with colitis surprisingly revealed a reduced Smad3 phosphorylation that was associated with an enhanced expression of Smad7 (FIGS. 2 and 3). In particular, FIG. 2 illustrates the presence of a band corresponding to the active (phosphorilated) Smad2/3 in LPMC isolated from the unaffected intestine but not from mice with TNBS-induced colitis. In the FIG. 3 it has been showed that the two bands, the lower 47 Kda band corresponding to the free Smad7 and the upper 102 Kda band corresponding to the TGF-$\beta$1

R1-Smad7 complex, are present only in LPMC specimens isolated from the intestine of mice with TNBS-induced colitis. These data indicate that local inflammation stimulates the synthesis of TGF-β1 which is not able to activate Smad signalling and dampen the mucosal inflammation.

According to the present invention it has been evaluated if treating TNBS mice with Smad7 antisense ODN could restore the endogenous TGF-β1 function and limit the ongoing inflammation.

First, it has been tested the efficacy of the above mentioned Smad7 antisense ODN (SEQ ID No 1 and SEQ ID No 4-15) to decrease Smad7 expression both in vitro and in vivo experiments.

As regards in vitro experiments, the LPMC isolated from the intestine of mice with TNBS-induced colitis were transfected with each of the Smad7 antisense ODN and incubated overnight. Smad7 analysis was carried out by Western blotting.

As regards in vivo experiments TNBS-treated mice were administered with Smad7 antisense ODN and after 3 days animals were sacrificed, tissue specimens were taken and Smad7 analysis was carried out by Western blotting.

Table 4 summarizes the results of these experiments and shows the percentage inhibition obtained by each Smad7 antisense oligonucleotide both in vitro and in vivo experiments. Data indicate mean±standard deviation (SEM) of four separate in vitro experiments and mean±SEM of five separate in vivo experiments.

TABLE 4

| Sequence (5'→3') | Site | % inhibition in LPMC | % inhibition in vivo | SEQ ID No |
|---|---|---|---|---|
| gtcgccccttctccccgcagc | 403 | 29 ± 3 | 33 ± 0.5 | 1 |
| MePgtMedcgccccttcc cMe-dcgcaMePg | 403 | 34 ± 1.5 | 55 ± 3 | 4 |
| gtt tgg tcc tga aca tgc | 294 | 26 ± 2.6 | 25 ± 3.4 | 5 |
| gtt tgg tcc tga acat | 296 | 16 ± 2 | 15 ± 3.2 | 6 |
| gtt tgg tcc tga acatg | 295 | 17 ± 3.1 | 10 ± 1.12 | 7 |
| agc acc gag tgc gtg agc | 577 (*) | 27 ± 0.88 | 25 ± 2.7 | 8 |
| MePagcacMedc gag tgMedc gtg agcMeP | 577 (*) | 29 ± 1.65 | 30 ± 1.3 | 9 |
| cga aca tga cct ccg cac | 233 (**) | 33 ± 2.3 | 32 ± 1.89 | 10 |
| Me-d cga aca tga cct cMe-d cg cac | 233 (**) | 36 ± 1.5 | 34 ± 2.2 | 11 |
| gtMedcgccccttctcccMe dcgcag | 403 | 32 ± 4.1 | 42 ± 1.8 | 12 |
| gatcgtttggtcctgaa | 299 | | | 13 |
| atcgtttggtcctgaac | 298 | | | 14 |
| MePgtMedcgccccttctcc cMedcgcaMePgc | 403 | 34 ± 1.6 | 56 ± 3 | 15 |

(*) Sequences No 16 and (**) No 12 of the U.S. Pat. No. 6,159,697 by ISIS.

All the antisense ODN were effective in reducing Smad7 expression when transfected in vitro in LPMC isolated from TNBS-treated murine models. From the analysis of the value of percentage inhibition shown in Table 4 it is remarkable that antisense oligonucleotidic sequences SEQ ID No 4, 10, 11, 12 and 15 showed the major efficacy.

Nevertheless, the percentage of Smad7 expression inhibition obtained by in vivo treatment with oligonucleotidic sequences SEQ ID No 10 and 11 did not significantly differ from that documented in vitro experiments.

Instead, treatment of mice with antisense ODN SEQ ID No 4 and 12 and 15 resulted clearly in a greater percentage of Smad7 inhibition than that obtained in vitro experiments, that is 55% vs 34%, 42% vs 32% e 56% vs 34% respectively (P<0.01).

In contrast, treatment of mice with antisense oligonucleotide SEQ ID No 7 caused a reduction in Smad7 expression in vivo which was of lower entity than that resulting when the antisense oligonucleotide was transfected in LPMC in vitro, that is 10% vs 17%, P<0.01.

Overall, these results suggest that only specific modifications into a Smad7 antisense ODN sequence are able to improve its pharmacokinetic, biochemical and biophysical profile.

No sign of acute toxicity was documented in mice receiving antisense oligonucleotides (SEQ ID No 1 and SEQ ID No 4-15). One out of 5, treated with TNBS, died after 3 days (20%). Similarly, ⅕ of mice receiving the Smad7 sense oligonucleotide died after 4 days.

No mortality was documented in mice group treated with Smad7 antisense ODN SEQ ID No 1 and SEQ ID No 4-15.

The use of antisense ODN sequences SEQ ID No 13 and SEQ ID No 14 is associated with a reasonable in vitro inhibition activity (11% and 9.5%, respectively). Nevertheless, the in vivo administration of such sequences was unexpectedly joined with a marked deterioration of the colitis, up to cause the death of all the mice after 72 hours of treatment.

Macroscopic analysis of the intestinal samples taken from these mice has revealed the presence of a severe colitis and this was associated to a substantial increase in the intestinal Smad7 expression.

As above said, it was tested the efficacy of Smad7 antisense ODN to limit the ongoing inflammation. For this purpose, mice after induction of colitis were administered with antisense oligonucleotides SEQ ID No 1, 4, 5 and 15 considering 5 animals for each group.

Following the treatment with Smad7 antisense ODN it has been revealed a reduction of the mucosal inflammation. This result was particularly evident in mice treated with antisense oligonucleotides 4 and 15. Indeed, the colitis severity of grade 3-4 in mice with colitis not receiving antisense reached grade 2 or 3 after administration of antisense oligonucleotide sequences 1 or 5 respectively, while in mice treated with oligonucleotidic sequences 4 or 15, inflammation has not exceeded grade 1.

To examine if Smad7 antisense oligonucleotides were effective also when administered orally, mice with TNBS-induced colitis were treated the day after the induction of colitis with Smad7 antisense oligonucleotide 4 or 15 or control (sense).

For this purpose oligonucleotides were risuspended in a bicarbonate solution. The final volume of the solution administered to each mouse was of 350 μl and contains doses of oligonucleotide equivalent to 250, 500 or 1000 μg. Such solution was administered per os through a catheter.

At fifth day mice were sacrificed and analysis of Smad7 expression and of inflammation degree were evaluated as indicated in the previous paragraphs. All the mice treated with antisense oligonucleotide, and not with the control sense oligonucleotide, showed a meaningful reduction of Smad7 expression ad an increased Smad3 phosphorylation, independently from the dose of the oligonucleotide being used.

Figure 4:
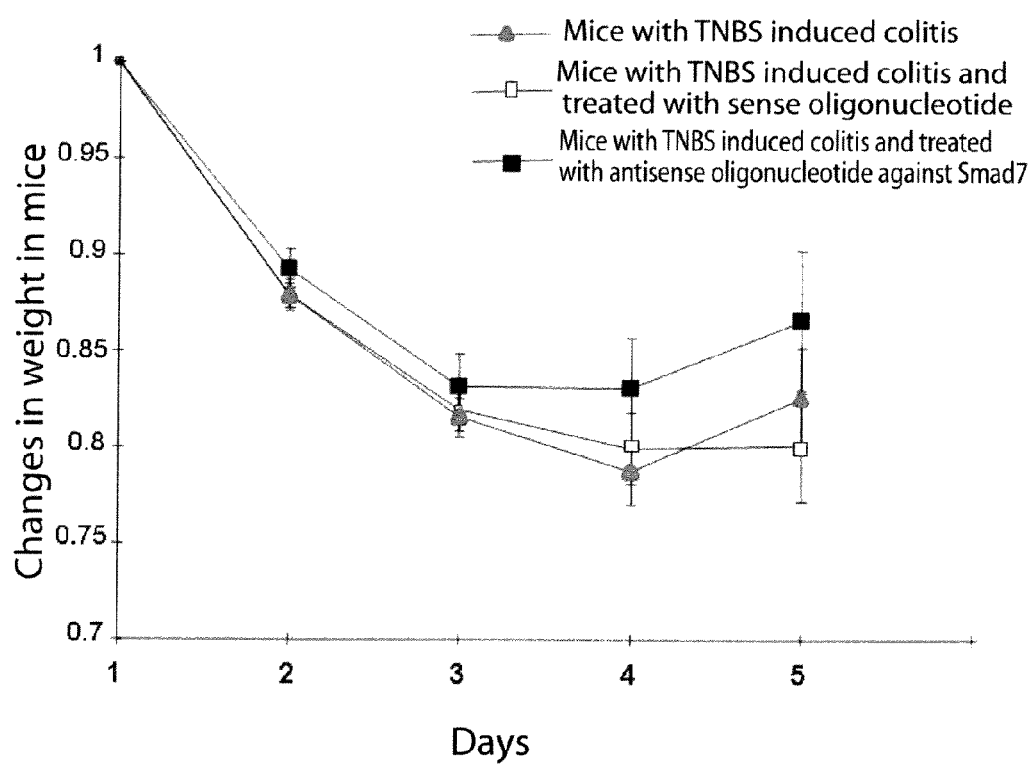
FIG. 4 shows the percentage changes in weight of mice with TNBS-induced colitis treated or not with Smad7 antisense oligonucleotide MePGTMe-dCGCCCCTTCTC-CCMe-dCGCAMePGC (SEQ. ID No 15) or with a control (sense); the figure is representative of three separate experiments wherein fourteen mice for each group have been studied.

Substantially, Smad7 inhibition was associated with a weight recovery as shown in FIG. 4. The FIG. 4 exhibits a graph which shows the percentage change in weight of the mice with TNBS-induced colitis treated or not treated with Smad7 antisense oligonucleotide (SEQ. N. 15) or control (sense). Both oligonucleotides were administered per os at the dose of 250 μg through catheter two days after the induction of colitis. The weight loss documentable at the second day in each of the three groups indicates that the treatment with TNBS induced colitis. Further it was proved that starting from the fourth day mice treated with Smad7 antisense oligonucleotide, but not with the control, showed a body weight recovery. The apparent and slight recovery seen at the fifth day in mice with TNBS-induced colitis is due to the fact that the 21.4% of mice with colitis died at the fourth day and therefore they were not considered in the evaluation of the body weight at the fifth day.

Figure 5:
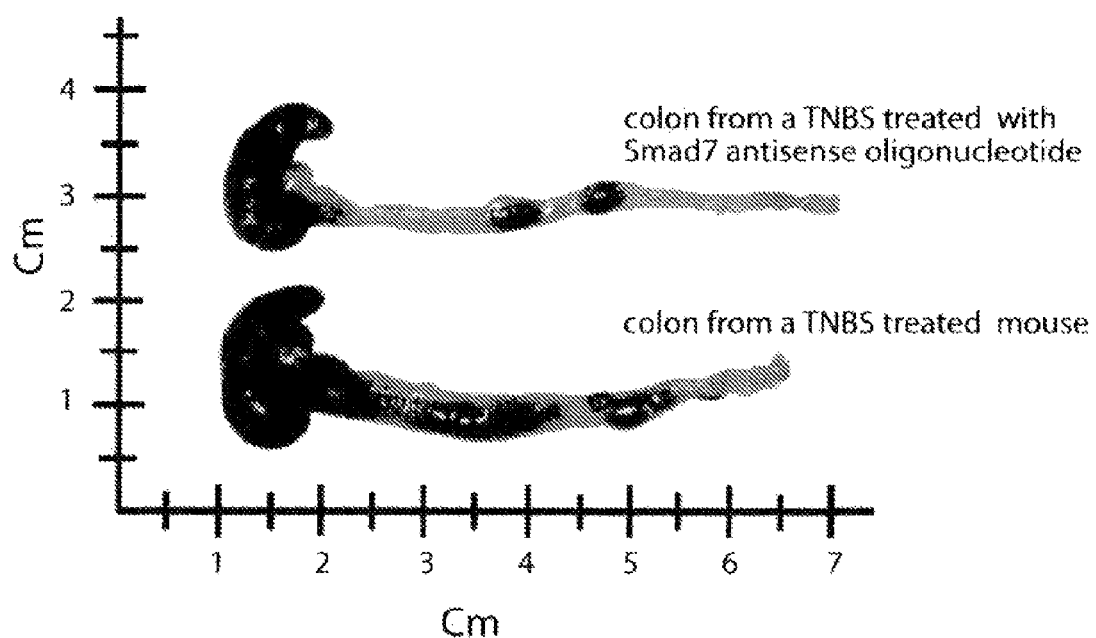
FIG. 5 shows macroscopic aspect of the colon extracted from a mouse with TNBS-induced colitis and from a mouse with TNBS-induced colitis treated with Smad7 antisense oligonucleotide (SEQ. ID No 15); the figure is representative of three separate experiments wherein fourteen mice for each group have been studied.

Smad7 inhibition was correlated to a marked suppression of tissutal inflammation as shown in FIGS. 5 and 6. FIG. 5 exhibits the images of the colon extracted from a mouse with TNBS colitis and from a mouse with TNBS colitis treated with Smad7 antisense oligonucleotides (SEQ. ID No 15). The oligonucleotide was administered per os at the dose of 250 µg through a catheter, at the second day after the induction of colitis. It has been showed that the colon from the mouse with TNBS-colitis is highly inflamed, shortened and thickening. On the contrary, the mouse receiving Smad7 antisense shows a colon of normal length and thickness and no macroscopic signs of phlogosis. FIG. 6 exhibits histological aspect of a colon section from a mouse without colitis or from mice with TNBS-colitis treated or not treated with Smad7 antisense oligonucloetide (SEQ ID No 15) or the control (sense). Both oligonucleotides were administered per os at the dose of 250 µg through catheter the second day after the induction of colitis. It has been shown that in the mouse without colitis, glands appear rectilinear and uniform with a normal content of muciparous cells and inflammatory elements of lamina propria. On the contrary, in the colon of TNBS treated mice receiving or not the control oligonucleotide, there was a total destruction of the glandular structure, with a muciparous and a massive inflammatory cells infiltration in the lamina propria. In the colic section of the mouse treated with TNBS and receiving Smad7 antisense oligonucleotide the presence of a normal glandular structure and the absence of phlogosis were demonstrated.

Together these observations suggest that the use of antisense ODN, which show the higher efficacy of Smad7 inhibition accompanied by the absence of side effects, following the in vivo administration, can represent a promising therapeutic strategy in the control of mucosa inflammation during IBD, especially if such characteristics of efficacy and toxicity were compared with the results achieved with other antisense ODN sequences with the same efficacy in the Smad7 in vitro inhibition.

EXAMPLE 3

In Vivo and In Vitro Studies on the Effects of the Administration of Smad7 Antisense Oligonucleotide (SEQ ID No:16) in the Context of Acute (TNBS- and Oxazolone-Colitis), Relapsing (TNBS) and Long Term (SCID Transfer Colitis) Inflammation in Mice In the present experiment the inventor examined TGF-β1 signaling in the context of acute (TNBS- and oxazolone-colitis), relapsing (TNBS) and long term (SCID transfer colitis) inflammation in mice. In these conditions it was found that induction of colitis is accompanied by abundant local TGF-β1 production associated with high Smad7 that, as in humans, blocks TGF-β1 signaling. However, administration of Smad7 anti-sense oligonucleotides, such as GTXGCCCCTTCTCCCXGCAGC, wherein X is 5-Me-dC (5-methyl 2′-deoxycitidine 5′-monophosphate) (SEQ ID NO:16) relieves the Smad7 block and enables TGF-β1 signaling and amelioration of disease. In fact, with respect to TGF-β1 signaling and Smad7 expression, acute and relapsing models of colitis reproduce the findings observed in humans IBD and that Smad7 anti-sense oligonucleotide may therefore have an important place in IBD therapy.

Materials and Methods

Induction of TNBS- and Oxazolone-Colitis

Studies of acute hapten-induced colitis were performed in 5-6 week old male SJL mice (Harlan Laboratories, S. Pietro al Natisone, UD, Italy), and maintained in the animal facility at the Istituto Superiore di Sanità, Rome, Italy. All studies were approved by Animal Care and Use Committee of Istituto Superiore di Sanità and Italian Ministry of Health. For induction of colitis, 2.5 mg of TNBS or 6 mg of oxazolone (Sigma-Aldrich, Milan, Italy) in 50% ethanol was administered to lightly anesthetized mice through a 3.5 F catheter inserted into the rectum. The catheter tip was inserted 4 cm proximal to the anal verge, and 150 µl of fluid was slowly instilled into the colon, after which the mouse was held in a vertical position for 30 seconds. Controls consisted of mice treated with 150 □l of 50% ethanol and untreated naive mice. Weight changes were recorded daily to assess the induction of colitis and tissues were collected for histologic study and protein analysis. For histological analysis tissues were fixed in 10% neutral buffered formalin solution, embedded in paraffin, cut into tissue sections and stained with hematoxylin and eosin (H&E). For TNBS-colitis stained sections were examined for evidence of colitis and assigned a colitis score by considering the presence of acute and chronic inflammatory infiltrates, elongation and/or distortion of crypts, frank ulceration, and thickening of the bowel wall, as described elsewhere (Goreli L, et al., 2002). For oxazolone-induced colitis, stained sections were examined and assigned a colitis score by examining the slide for the presence of hypervascularization, mononuclear cells, epithelial hyperplasia, epithelial injury, and granulocytes (Boirivant M, et al., 1998; Boirivant M, et al., 2001; Lawrance I C, et al., 2003).

Colitis was assessed as described elsewhere (Lawrance I C, et al., 2003). Briefly, serial paraffin sections of the colon were stained with H&E, and the degree of inflammation was scored as absent, mild, moderate, or severe based on the density and extent of both the acute and chronic inflammatory infiltrate, loss of goblet cells, and bowel wall thickening. An inflammatory infiltrate of low cellularity confined to the mucosa was scored as mild inflammation, and transmural inflammation with extension into the pericolonic adipose tissue with high cellularity was scored as severe. Intermediate changes were scored as moderate inflammation. SCID model of colitis: colitis was induced in SCID mice according to the protocol described by Read and Powrie (Read S, et al., 1999). Development of colitis was monitored by weekly record of the body weight and presence of loose stools. Diagnosis of colitis was made by histological analysis of the colon.

Inhibition of Murine Smad7 Production by Smad7 Antisense Oligonucleotide

To evaluate the ability of Smad7 antisense to inhibit Smad7, murine macrophage cell lines (RAW cells) were transfected with Smad7 antisense or sense oligonucleotides (2 µg/ml; GTXGCCCCTTCTCCCXGCAGC, wherein X is 5-Me-dC (SEQ ID NO:16)) by lipofectamine for 48 hours. The cells were then harvested and subjected to Western blot analysis of Smad7. The efficiency of the transfection was determined with a fluorescein-labelled Smad7 antisense oligonucleotide and transfection rate was evaluated by performing flow cytometry and fluorescent microscopy 24 hours after transfection. The same fluorescein-labelled Smad7 antisense oligonucleotide was used to assess the in vivo uptake of the orally administered oligonucleotide. To this end, mice with TNBS-colitis were given fluorescein-labelled antisense DNA (125 µg/mouse) by oral administration 1 day after TNBS injection and then sacrificed 0, 4, 8, 16, 24 and 48 hours later. At each time point, stomach, small intestine, colon, liver, spleen, and kidney were collected, cut in sections and analyzed by fluorescent microscopy.

To examine the therapeutic effect of Smad7 antisense oligonucleotide (GTXGCCCCTTCTCCCXGCAGC, wherein X is 5-Me-dC (SEQ ID NO:16)) on the course of ongoing intestinal inflammation, mice were treated with a single dose of Smad7 antisense or sense oligonucleotide (from 50, 125 or 250 µg/mouse) in 500 µl of bicarbonate solution (pH 9.5) by oral administration on the day after the induction of colitis. The mice were then monitored daily for weight changes and then sacrificed 3 (TNBS-colitis) and 2 (oxazolone colitis) days after oligonucleotide administration. To evaluate the effect of Smad7 antisense oligonucleotide administration on relapsing TNBS-colitis in BALB/c mice, mice were divided into two groups the day after the final TNBS administration: one group was treated with Smad7 antisense oligonucleotide and the other with sense oligonucleotide (125 µg/mouse, on days 1 and 3 after the last TNBS dose). Weight changes were recorded daily and mice were sacrificed at day 6.

To evaluate the effect of Smad7 antisense oligonucleotide (SEQ ID No:16) on SCID model of colitis, 6 weeks after cell transfer the mice were treated with oral Smad7 anti-sense or sense oligonucleotide (125 µg/mouse) and weight changes were recorded on day 1, 3, 7 and 10 after treatment.

Isolation of Lamina Propria Mononuclear Cells (LPMC)

LPMC were isolated as described in the previous example or by cell sorting after staining cells with anti-mouse CD3-FITC (BD Pharmingen) using a FACS-ARIA. Purity of CD3+ cells was confirmed by flow cytometry and was consistently higher than 95%.

Determination of Cytokine Secretion by ELISA

Total protein extracts were prepared as previously described in the above examples. Briefly, snap frozen mucosal samples or cells were homogenized in buffer containing 10 mM Hepes (pH 7.9), 10 mM KCl, 0.1 mM EDTA, and 0.2 mM EGTA, supplemented with 1 mM dithiothreitol (DTT), 10 µg/ml aprotinin, 10 µg/ml leupeptin, and 1 mM phenylmethanesulphonyl fluoride (Sigma).

Western Blotting

Western blotting for the detection of p-Smad3, Smad7 were performed as above described.

Statistical Analysis

The significance of differences between groups was determined using either the Mann-Whitney U test or Student t test.

Results

It has been shown that TNBS-colitis is characterized by decreased p-Smad3 and increased Smad7 expression. Particularly, levels of activated TGF-β1 were higher in extracts from mice with TNBS-colitis (median: 56.5; range: 44-83 pg/100 µg total proteins) than those from untreated (median: 8.2; range: <10-19 pg/100 µg total proteins, p=0.03) or ethanol-treated mice (median: 19; range: <10-28 pg/100 µg total proteins, p=0.04). Since activated TGF-β1 is generated in the extracellular space, this indicates that increased amounts of TGF-β1 is secreted as well as synthesized in TNBS-colitis.

In a complementary analysis, TGF-β1 was analyzed in extracts of epithelial cells. Colonic epithelial cells from mice treated with TNBS contained higher levels of TGF-β1 (44±7 pg/100 µg total proteins) than those measured in extracts of ethanol-treated mice (35±2.5 pg/100 µg total proteins), but the difference was not statistically significant. The lack of statistical significance could rely on the fact that the isolated colonic cells undergo rapid apoptosis. Taken together, these data show that TNBS-colitis is associated with a significant increase in TGF-β1 production that is, at least in part, derived from epithelial cells.

Administration of Smad7 Antisense Oligonucleotide Inhibits Smad7 Protein Expression and Restores TGF-β1 Signaling in TNBS-Colitis The above data prompted us to explore the possibility that in TNBS-colitis, high local Smad7 blocks the immunosuppressive activity of the endogenous TGF-β1 and thus contributes to ongoing intestinal inflammation. Thus, it was determined whether the administration of Smad7-specific antisense oligonucleotide (GTXGCCCCTTCTCCCXGCAGC, wherein X is 5-Me-dC (SEQ ID NO:16)) could affect the course of experimental colitis. In these studies, RAW cells constitutively expressing Smad7 were transfected with Smad7 antisense or sense oligonucleotides and then assessed for Smad7 protein expression by Western blotting. Using a fluorescein-labeled Smad7 antisense DNA to identify transfected cells by flow cytometry, almost ⅔ of the RAW cells were efficiently transfected (FIG. 7A). In addition, the transfected cells exhibited a marked decrease in Smad7 expression (FIG. 7A, right inset). These results led us to determine the ability of this oligonucleotide to inhibit Smad7 in vivo. Initially, we administered fluorescein-labelled Smad7 antisense oligonucleotide to mice with TNBS-colitis at day 1 after colitis induction by oral gavage in order to determine the tissue distribution of oligonucleotide administered by this route. Administration by oral gavage was selected so as to target the mucosal tissues rather than systemic tissues and thus to minimize potential adverse effects. Fluorescein-label oligonucleotide was seen in both the small intestinal and colonic lamina propria and epithelial layer at 4, 8 (FIG. 7B) and 16 hours after oligonucleotide administration and then disappeared at 24 and 48 hours after administration (not shown). Finally, it was determined whether administration of Smad7 antisense oligonucleotide administered by oral gavage affected Smad7 and p-Smad3 expression in the colon of mice with TNBS-colitis. Administration of Smad7 antisense but not sense oligonucleotide significantly reduced Smad7 (p=0.02) and enhanced p-Smad3 (p=0.03) (FIG. 7C).

Orally Administered Smad7 Antisense Oligonucleotide Ameliorates Acute TNBS-Colitis Therapeutic effectiveness of Smad7 antisense oligonucleotide (GTXGCCCCTTCTCCCXGCAGC, wherein X is 5-Me-dC (SEQ ID NO:16)) in mice with acute TNBS-colitis was assayed. Mice administered Smad7 antisense oligonucleotide as a single oral dose of 125 or 250 µg/mouse (but not 50 µg/mouse) on day 1 after induction of TNBS-colitis exhibited an initial weight loss which rapidly stabilized so that by day 4 the weight loss in the treated group was clearly lower than in the untreated group (p<0.01) (FIGS. 8A and B), and by day 7 it was not different from the initial weight (not shown). In addition, as shown in FIG. 8C, histologic examination of colon tissue as well as blinded histologic scoring of colitis in the different groups were significantly reduced in antisense-treated mice as compared to untreated or sense-treated mice (p<0.01). Then, it was determined the effect of orally administered Smad7 antisense oligonucleotide (again given as a single 125 µg dose on day 1 after TNBS-colitis induction) on cytokine production in mice with TNBS-colitis. Administration of Smad7 antisense but not sense oligonucleotide to mice with TNBS-colitis significantly reduced the colonic production of both IL-12 and IFN-γ (p<0.03) (FIG. 9 A, B, C).

Administration of Smad7 Antisense Oligonucleotide Ameliorates Oxazolone Colitis

Next the effect of Smad7 inhibition on oxazolone colitis by administration of Smad7 antisense oligonucleotide (GTXGCCCCTTCTCCCXGCAGC, wherein X is 5-Me-dC (SEQ ID NO:16)) was determined. The oligonucleotides were administered by oral gavage 1 day after the induction of colitis, and mice were sacrificed at day 3. Analysis of Smad7 expression showed a marked reduction in the colon of mice treated with the antisense but not sense oligonucleotide, and this was associated with increased p-Smad3 (FIGS. 10A and B, p=0.03). Moreover, mice treated with the Smad7 antisense oligonucleotide exhibit less weight loss and less mortality than those treated with sense oligonucleotide: the mean weight observed at day 3 was 90.3%±2.8 and 84.7%±1.7 of baseline in mice treated with the antisense or sense oligonucleotide respectively and corresponding mortality figures were 0% and 21.4% of mice. These data were consistent with histologic study of tissues in that Smad7 antisense but not sense oligonucleotide led to markedly decreased inflammation (FIG. 10C).

Smad7 Antisense Oligonucleotide Reverses Relapsing TNBS-Colitis

In further studies, we examined whether the Smad7 antisense oligonucleotide (GTXGCCCCTTCTCCCXGCAGC, wherein X is 5-Me-dC (SEQ ID NO:16)) could reverse relapsing colitis by the use of a TNBS-colitis model. In this model the mice lost weight during the first 1-2 days following each TNBS instillation but then regained the same or more weight before the next instillation a week later; thus, the average weight of mice in the group administered TNBS was similar to those in the group not administered TNBS at the time of fourth and final treatment. It should be noted that although the mice in this model had persistent inflammation, the latter was being maintained by weekly TNBS administration and thus could be considered as a colitis characterized by persistent inflammation with recurrent relapses of acute inflammation. Histological examination of the colons obtained from mice one day after the fourth weekly instillation of TNBS revealed that 15% of mice developed a severe inflammation, while 70% and 15% of mice had a moderate or mild colitis respectively (FIG. 11A). In addition, Western blot analyses of extracts from the inflamed colons of TNBS-treated mice exhibited reduced p-Smad3 and increased Smad7 as compared with extracts of control mice (FIG. 11B), Up-regulation of Smad7 was seen both in CD3+ and CD3-negative LPMC isolated from mice with established TNBS-induced colitis (FIG. 11B, right inset). Finally, to examine if treatment of mice with Smad7 oligonucleotide could reverse the mucosal inflammation present after the fourth instillation of TNBS, Smad7 anti-sense oligonucleotide was administered to mice by oral gavage on days 1 and 3 after the last (4$^{th}$) TNBS instillation. Mice treated with Smad7 antisense oligonucleotide lost only 2% of body weight by day 2 after the first Smad7 antisense oligonucleotide administration, regained all of the weight lost by day 3, and were above baseline weight by day 6. (FIG. 11C). In contrast, mice treated with sense oligonucleotide exhibited a significantly greater loss of weight and did not fully reach baseline weight by day 6 (FIG. 11C). In mice treated with the above antisense oligonucleotide, Smad7 was reduced both in CD3+ and CD3-negative LPMC (FIG. 7C, right inset). Histological examination of colons of mice treated with anti-sense oligonucleotide showed that 45% of mice exhibited mild colitis while 55% of them had no evidence of inflammation. In contrast, all mice treated with sense oligonucleotides exhibited moderate (80%) or mild (20%) colitis (FIG. 11D). These data suggest that Smad7 anti-sense oligonucleotide can interrupt and reverse the course of a relapsing colitis.

BIBLIOGRAPHY

Podolsky D. K., N. Engl. J. Med., 2002 Ago; Vol. 347: No 6.
Seegers D. et al. Aliment. Pharmacol. Ther., 2002; Vol. 16: 53-58.
Sandborn J., et al. Gastroenterology, 2002 Mag; Vol. 122: No 6.
Fiocchi C., J. Clin. Invest., 2001 Ago; Vol. 108: 523-526.
Powrie F., et al. J Exp Med 1996; 183: 2669-2674.
Neurath M. F., et al. J Exp Med 1996; 183: 2605-2616.
Ludviksson B. R., et al. J Immunol 1997; 159: 3622-3628.
Shull M. M., et al. Nature 1992; 359: 693-699.
Christ M., et al. J Immunol 1994; 153: 1936-1946.
Hahm K. B., et al. Gut. 2001; 49:190-198.
Gorelik L., et al. Immunity 2000; 12: 171-181.
Heldin C-H., et al. Nature 1997; 390: 465-471.
Yang X., et al. Embo J 1999; 18: 1280-1291.
Hayashi H., et al. Cell 1997; 89: 1165-1173.
Lawrance I C. et al. Inflamm Bowel Dis 2001; 7:16-26.
Monteleone G., et al. J. Clin. Invest., 2001 Giu; Vol. 108:601-609.
Boirivant M., et al. *Gastroenterology* 1999; 116: 557-565.
Han S H., et al. J Pharmacol Exp Ther. 1998; 287:1105-12.
Arsura M., et al. Immunity 1996; 5: 31-40.
Brevetto statunitense U.S. Pat. No. 6,159,697.
Maggi A., Biotecnologie Farmacologiche, 1998; Cap. 8: 125-131.
Agrawal S., Molecular Medicine Today, 2002; Vol. 6: 72-81.
Neurath M., Fuss I., Strober W., Int Rev Immunol., 2000; Vol. 19: 51-62.
Lesiak K. et al., Bioconjugate Chem., 1993; Vol. 4: 467.
Xiao W. et al. Antisense Nucleic Acid Drug Dev., 1996; Vol. 6: 247-258.
Sanghvi et al, Nuclei Acids Research, 1993; Vol. 21: 3197-3203.
Maier M A. et al. Org Lett., 2002; Vol. 2: 1819-1822.
Guerlavais T., et al. Anal Bioanal Chem., 2002; Vol. 374: 57-63.
Ragas J. A., et al. Analyst., 2000; Vol. 125: 575-581.
Goreli L, Flavell R A. Nature Rev. Immunol. 2002; 2: 46-53.
Neurath M F, Fuss I, Kelsall B L, Presky D H, Waegell W, Strober W. J. Exp. Med. 1996; 183: 2605-2616.
Boirivant M, Fuss I J, Chu A, Strober W. J. Exp. Med. 1998; 188: 1929-1939.
Boirivant M, Fuss I J, Ferroni L, De Pascale M, Strober W. J. Immunol. 2001; 166: 3522-3532.
Lawrance I C, Wu F, Leite A Z, Willis J, West G A, Fiocchi C, Chakravarti S. Gastroenterology 2003; 125:1750-1761.
Read S, Powrie F. In: Coligan J E, Kruisbeek A M, Margulies D M, Shevach E M, Strober W, ed. Current Protocols in Immunology. 15.13. John Wiley & Sons, Inc, 1999: 1-10.

The invention claimed is:

1. An antisense oligonucleotide against SMAD7 comprising SEQ ID NO: 9 (5'-YGCACXGAGTGXGTGAGZ-3'), wherein X is 5-methyl-2'-deoxycytidine 5'-monophosphate, Y is 2'-deoxyadenosine methylphosphonate, and Z is 2'-deoxycytidine methylphosphonate, or complements thereof.

2. A method of treating ulcerative colitis, comprising administering to a patient in need thereof an effective amount of the antisense oligonucleotide of claim 1.

3. A method of treating inflammatory bowel disease, comprising administering to a patient in need thereof an effective amount of the antisense oligonucleotide of claim 1.

* * * * *